United States Patent [19]
Lucá

[11] Patent Number: 5,132,113
[45] Date of Patent: Jul. 21, 1992

[54] NUTRITIONAL COMPOSITION CONTAINING ESSENTIAL AMINO ACIDS

[76] Inventor: Maurizio Lucá, Corso Francia, 206 Int. 7, Rome, Italy

[21] Appl. No.: 604,665

[22] Filed: Oct. 26, 1990

[51] Int. Cl.$^5$ .......................... A61K 35/78; A23L 1/30
[52] U.S. Cl. ................................. 424/195.1; 426/74; 426/72
[58] Field of Search ............... 426/72, 73, 74; 514/23, 514/52, 909; 424/195.1

[56] References Cited

U.S. PATENT DOCUMENTS

| | | | |
|---|---|---|---|
| 3,697,287 | 10/1972 | Winitz | 99/1 |
| 4,029,773 | 6/1977 | Beigler | 424/180 |
| 4,070,488 | 1/1978 | Davis | 426/72 |
| 4,220,666 | 9/1980 | Fields | 426/62 |
| 4,268,529 | 5/1981 | Davis | 426/72 |
| 4,357,343 | 11/1982 | Madsen | 424/274 |
| 4,710,387 | 12/1987 | Uiterwaal | 426/72 |
| 4,833,128 | 5/1989 | Solomon | 514/23 |

OTHER PUBLICATIONS

Chemical Abstracts, vol. 112 No. 5, Jan. 29, 1990, 112:42590d.
Amino Acid Infusion Solution; Ajinomoto Co., Inc.
Amino Acids–Tables and Charts; Ajinomoto Co., Inc. (1982).
Energy and Protein Requirements; Word Health Organization (1985) pp. 120–129.

*Primary Examiner*—Ronald W. Griffin
*Assistant Examiner*—Ralph Gitomer
*Attorney, Agent, or Firm*—Hedman, Gibson & Costigan

[57] ABSTRACT

A nutritional composition is disclosed which is based on essential amino acids.

24 Claims, No Drawings

NUTRITIONAL COMPOSITION CONTAINING ESSENTIAL AMINO ACIDS

BACKGROUND OF THE INVENTION

Human nutrition requires a source of the components of protein, carbohydrates, lipids, vitamins and minerals. Many and varied sources for these nutrient materials have been utilized in the prior art. The prior art does not disclose the concept of providing a balanced supply of nutrients which permits substantially complete absorption of the nutrients which are administered to an individual.

Proteins are associated with all forms of life, an observation that dates back to the original identification of protein as a class by Mulder in 1838. The proteins of living matter act as organic catalysts (enzymes), as structural features of the cell, as messengers (peptide hormones), and as antibodies. The importance of protein in the diet is primarily to act as a source of amino acids, some of which are essential (indispensable) dietary constituents because their carbon skeletons are not synthesized in the bodies of animals. It is known that the adult human requires eight amino acids which are essential for the maintenance of good health. These amino acids are isoleucine, leucine, lysine, methionine, phenylalanine, threonine, tryptophan and valine.

Amino acid solutions are commercially available for nutrient I.V. feeding of post operative patients, pediatric patients, patients with renal failure and patients with hepatic failure. The available amino acid I.V. solutions are based on crystalline amino acids which have an advantage over the amino acids solutions which were obtained by hydrolysis of proteins such as fibrin or casein. These solutions were nutritionally incomplete in the amino acid content and caused toxic reactions which led to the banning of these solutions in the United States by the Food and Drug Administration.

Amino acid solutions are available which contain all of the essential amino acids in combination with non-essential amino acids, with or without vitamins, minerals and a carbohydrate and fat source.

To estimate the nutritional value of protein as well as amino acid formulas, the accepted methodology is to determine, during the ingestion of a protein(s) or an amino acid formula, the subject's nitrogen balance. This represents the difference between nitrogen intake and nitrogen output, the difference being either positive (nitrogen retention, as in active growth), negative (nitrogen loss), or zero (nitrogen equilibrium).

In order to carefully determine nitrogen balance (nitrogen intake - nitrogen output), I have used the formula:*

$$B = I - (U + F + S)*$$

where:
B = Nitrogen Balance
I — Nitrogen Intake
U = Nitrogen Loss In Urine
F = Nitrogen Loss In Feces
S = Nitrogen Dermal Losses This formula has been used to compute the Net Nitrogen Utilization (NNU) for the amino acid formulas and proteins that were tested.

* Munro, H.N., Crim M.C., in "Modern Nutrition In Health and Disease" Shils, M.E., Young, V.R. (Eds), page 24, Lea & Febiger, Philadelphia 1988

The prior art amino acid solutions, which have widely different ratios of the component amino acids, have not been found to be suitable as total nutrient compositions because after prolonged reliance on these compositions, symptoms of nutrient deficiency are detected due to the low percentage of their net nitrogen utilization (NNU). The low net nitrogen utilization (NNU) results in the presence of unabsorbed amino acids, which are deaminated and cause an increased production of blood urea nitrogen (BUN) as well as increased levels of other metabolic nitrogen containing products. This problem is particularly difficult with patients who have renal failure and/or hepatic disorders.

U.S. Pat. No. 3,697,287 disclose an amino acid food composition which is described as a palatable mixture of the essential and non-essential amino acids, minerals, vitamins, carbohydrates and fats. That composition contains essential and non-essential amino acids. The essential amino acids in such a composition are present in the following ratios:

| | |
|---|---|
| L-valine | 1.0 |
| L-arginine | 1.77 |
| L-isoleucine | .91 |
| L-lysine | 1.03 |
| L-phenylalanine | 1.03 |
| L-histidine | .44 |
| L-leucine | 1.43 |
| L-methionine | .93 |
| L-threonine | .91 |
| L-tryptophan | .28 |

I have discovered that the use of an amino acid composition which contains specific proportions of the essential amino acids will make possible a higher NNU as compared to high NNU protein such as hen whole egg protein or other amino acid compositions. I have discovered that the oral administration of a composition which consists of essential amino acids will result in a higher NNU as compared to compositions which also include non-essential amino acids. In addition, the use of a preferred embodiment of the invention, will avoid causing or unduly exacerbating the BUN of patients in which the nitrogen intake is required to be restricted who are fed with certain of the applicant's composition. The avoidance of exogenous residual nitrogen is achieved by the formulation of the amino acid composition with a specific ratio of the essential amino acids which provide for substantially complete absorption of the required quantity of the amino acids. The novel amino acid composition of the invention may be utilized alone or in combination with carbohydrates, lipids, vitamins and minerals depending on the particular nutrient requirements of a particular patient.

I have also discovered that the feeding of the amino acid composition of the invention has a profound immunostimulant effect which can be determined by the means of objective clinical criteria.

The main function of dietary carbohydrate is to provide energy. Administration of carbohydrate has long been known to spare protein in early fasting.

Protein is abruptly lost upon initiating a fast or upon withdrawing carbohydrates from an adequate diet (even if replaced isoenergetically by fat). Glucose is the main carbohydrate in the body and although glucose can be utilized by all cells, it is essential only in a few organs, including the brain and the red cells. Although glucose can be converted to fat, it should be noted that fat cannot be converted to glucose. All the dietary carbohydrates seem to reduce the level of high-density lipoprotein (HDL) cholesterol in the serum, and HDL cholesterol:total cholesterol ratio in the serum is reduced to a greater extent by sucrose than by glucose. The type of dietary carbohydrate can alter the level of triglyceridemia, and this effect can be negated by the addition of polyunsaturated fat to the diet.

Dietary lipids consist mainly of triglycerides (TG), a useful and concentrated source of energy. An adequate TG supply and absorption are especially important for infants and also for adults with a high energy requirement, such as patients with major burns, malignant tumors, and surgical wounds. The alternative energy sources, protein and carbohydrates, deliver per gram, 4 Kcal, less than half the energy density of fats, and require bulky meals to cover high energy requirements. Essential Fatty Acids (EFA) are necessary for the normal function of all tissues, it is therefore not surprising that the list of symptoms of EFA deficiency is a long one. As no animal, including man, can synthesize EFA, it is completely dependent on vegetable lipids to meet EFA requirements.

It has been demonstrated convincingly that diets enriched in EFA such as linoleic acid and reduced in saturated fatty acids do lower significantly LDL and VLDL cholesterol in man at both 30 and 40 in % of fat levels (3).

I have discovered that the oral administration of a composition which contains specific proportion of protein-free carbohydrate and protein-free polyunsaturated vegetable fat results in a palatable mixture having the highest apparent digestibility (AD) a higher Energy Density per weight and per volume and a higher content in EFA joined with a lower content in saturated fatty acids of any natural food or palatable dietetic composition for use as a complement in feeding patients such as infants, alcoholics, drug abusers, Acquired Immune Deficiency Syndrome (AIDS) patients, Aids Related Complex (ARC) patients, cancer patients, psychiatric patients, geriatric patients and the like, who have an increased catabolism, and/or fail to eat, because of a physiological and/or psychological lack of appetite.

Each dietary fuel differs in apparent digestibility (%), which is calculated as:

$$\frac{(Intake-Stool\ losses)}{Intake} \times 100$$

To illustrate: If 100 grams of fat are ingested per day, and if the daily stool fat averages 5 grams, then the "apparent digestibility" (AD) of fat is 95%.

I have discovered that the oral administration of a composition which contains specific proportion of mineral-free, protein-free carbohydrate(s) and highly polyunsaturated vegetable fat(s) with the highest content in EFA join with the lowest content in saturated fatty acids, results in a palatable mixture which will avoid causing or unduly exacerbating the level of High-Density Lipoprotein (HDL), Low-density-Lipoprotein (LDL) and Very Low-Density-Lipoprotein (VLDL) cholesterol in the serum of patients in which HDL, LDL and VLDL cholesterol level is required to be restricted who are fed with certain of the applicant's composition.

I have also discovered that the oral administration of a composition which contains specific proportion of mineral free, protein-free carbohydrate and highly polyunsaturated vegetable fat results in a palatable mixture which will avoid causing or unduly exacerbating the Blood Urea Nitrogen (BUN) of patients in which nitrogen intake is required to be restricted who are fed with certain of the applicant's compositions.

I have also discovered a novel concept for providing vitamin and mineral requirements by means of a method which is based on the administration of an amount of vitamins and minerals which is proportionate to the amount of amino acid which are administered.

I also discovered an object of the invention to provide an improved palatable mineral free protein-free carbohydrate and highly polyunsaturated vegetable fat based nutrient composition.

It is also an object of the invention to provide a palatable protein-free carbohydrate and protein-free polyunsaturated fat based composition which is useful because of its highest apparent digestibility (AD) and energy density (ED) in the nutritional support of patients suffering from disease where restricted nitrogen intake is indicated such as in certain renal and hepatic dysfunctions.

It is also an object of the invention to provide a palatable mineral-free protein-free carbohydrate and protein-free highly polyunsaturated vegetable fat based composition a higher apparent digestibility (AD) and energy density (ED) content and a higher EFA content joined with a lower saturated fatty acid content of any natural food or palatable dietetic composition for use as a supplement in feeding patients such as infants, alcoholics, drug abusers, Acquired Immune Deficiency Syndrome (AIDS) patients, Aids Related Complex (ARC) patients, cancer patients, psychiatric patients, geriatric patients and the like, who have an increased catabolism, and/or who fail to eat, because of a physiological and/or psychological lack of appetite.

It is also an object of the invention to provide a mineral-free, protein-free carbohydrate and highly polyunsaturated vegetable fat based composition which has the advantage of low storage and shipping cost which may be used as an emergency food to be shipped by air in response to catastrophic events.

It is also an object of the invention to provide a method for increasing the energy density as well as the apparent digestibility (AD) as well as the EFA content of an unmodified foodstuff by selectively adding a palatable mineral-free, protein-free carbohydrate and highly polyunsaturated vegetable fat based composition, which are absent or are present at a low level, for the purpose of preparing a modified foodstuff which has a higher apparent digestibility (AD) and energy density and EFA content than the unmodified foodstuff.

It is also an object of the invention to provide a mineral-free, protein-free carbohydrate and highly polyunsaturated vegetable fat based composition for use in patients where mineral restriction is required such as cardiovascular patients and renal patients.

It is also an object of the invention to provide a mineral-free, protein-free carbohydrate(s) and highly polyunsaturated vegetable fat(s) based composition for use in patients where the level of HDL, LDL, and VLDL cholesterol level is required to be restricted.

It is also an object of the invention to provide a palatable mineral-free, protein-free carbohydrate(s) and highly polyunsaturated vegetable fat(s) based composition for use as a supplement, source and/or complement to foodstuffs such as milk, dry milk casein, soft drinks, alcoholic drinks, and the like to provide or increase the apparent digestibility (AD), and the energy density, and the EFA content.

It is also an object of the invention to provide a palatable mineral-free, protein-free carbohydrate(s) and highly polyunsaturated vegetable fat(s) based composition for use as a supplement, source and/or complement to foodstuffs such as milk, dry milk casein liquids, soft drinks, alcoholic drinks, and the like to provide or increase the apparent digestibility (AD) and the nutrients content.

It is also an object of the invention to provide a palatable mineral-free, protein-free carbohydrate(s) and highly polyunsaturated vegetable fat(s) based composition which is useful as a complement in the nutritional support of patients who are afflicted with malabsorption.

It is also an object of the invention to provide a palatable mineral-free, protein-free carbohydrate(s) and highly polyunsaturated vegetable fat(s) based composition which is useful in the treatment of Protein-Calorie Malnutrition (PCM).

It is also a primary object of the invention to provide an improved amino acid based nutrient composition.

It is also an object of the invention to provide an amino acid based composition which is useful because of its high NNU in the nutritional support of patients suffering from disease where restricted nitrogen intake is indicated such as in certain renal and hepatic dysfunctions.

It is also an object of the invention to provide an amino acid composition having the highest NNU and protein density (content per volume and per weight) of any natural protein food and/or other amino acid composition for use in feeding patients such as infants, alcoholics, drug abusers, Acquired Immune Deficiency Syndrome (AIDS) patients, Aids Related Complex (ARC) patients, cancer patients, psychiatric patients, geriatric patients, and the like, who have an increased catabolism and/or who fail to eat, because of a physiological and/or psychological lack of appetite.

It is also an object of the invention to provide an amino acid composition which has the advantage of low storage and shipping costs which may be used as an emergency food to be shipped by air in response to catastrophic events.

It is also an object of the invention to provide a method for increasing the amino acid content of an unmodified foodstuff by selectively adding amino acids which are absent or are present at a low level for the purpose of preparing a modified foodstuff which has a higher NNU than the unmodified foodstuff.

It is also an object of the invention to provide a amino acid based composition for use in infant nutrition.

It is also an object of the invention to provide an amino acid based composition which is useful in the treatment and prevention of severe and/or mild obesity as well as over weight.

It is also an object of the invention to provide an amino acid based composition which is useful for the treatment of metabolic anemias.

It is also an object of the invention to provide a mineral free, amino acid based composition for use in patients where mineral restriction is required such as cardiovascular patients and renal patients.

It is also an object of the invention to provide an amino acid based composition for use as a supplement, source and/or complement to foodstuffs such as flours, dry milk solids, casein liquids, soft drinks, alcoholic drinks and the like to provide or increase the net nitrogen utilization (NNU).

It is also an object of the invention to provide an amino acid based composition which is useful in the nutritional support of patients who are afflicted with malabsorption.

It is also an object of the invention to provide an amino acid based composition which has a ratio of essential amino acids that will provide a higher net nitrogen utilization (NNU) as compared to proteins having high NNU such as hen whole egg protein, casein protein, bovine dry milk proteins, soy protein, and the like.

It is also an object of the invention to provide an amino acid based composition which is useful in the treatment of Protein-Calorie Malnutrition (PCM).

These and other objects of the invention will become apparent from the appended specification.

SUMMARY OF THE INVENTION

The invention comprises a novel amino acid composition comprising a combination of the following essential amino acids:
isoleucine;
leucine;
lysine;
methionine;
phenylalanine;
threonine;
tryptophan; and
valine
in amounts relative to one another which will provide a net nitrogen utilization (NNU) of at least 75%, preferably or 90% and most preferably 95%. The composition may also contain carbohydrates, Essential Fatty Acid (EFA) sources, vitamins and/or minerals.

The amino acid composition has particular use in providing essential nutrients for the prevention or treatment of Protein-Calorie Malnutrition (PCM), in feeding patients such as infants, alcoholics, drug abusers, Acquired Immune Deficiency Syndrome (AIDS) patients, Aids Related Complex (ARC) patients, cancer patients, psychiatric patients, geriatric patients and the like, who have an increased catabolism and/or who fail to eat, because of a physiological and/or psychological lack of appetite.

In particular, the amino acid composition may also be used for supportive nutrition in the case of trauma due to burns, surgery or in diseases, such as kidney disorders, liver disorders, hypercholesterolemia, diabetes mellitus, gout, and the like. A specific application is in the treatment and prevention of obesity which has been successfully treated with certain preferred compositions of the invention.

The invention also comprises a novel palatable nutritional composition comprising a combination of a specific protein-free carbohydrate and specific protein-free polyunsaturated fat:

| | |
|---|---|
| protein-free carbohydrate | 70-95 wt. % |
| protein-free highly polyunsaturated vegetable fat | 5-30 wt. % |

These specific carbohydrate and specific polyunsaturated fat compositions may be used alone or in combination with the amino acid composition of the invention in amounts that vary according to the nutritional requirements of the patient. This may vary between 12 Kcal to 60 Kcal per gram of amino acids.

The preferred ranges are from 80-90 wt.%, protein-free carbohydrate and 20-10 wt.% highly polysaturated vegetable fat and the especially preferred ranges are respectively about 85 wt. % to about 15 wt. %.

The composition made by specific mineral-free, protein-free carbohydrate and specific highly polyunsaturated vegerable fat, in amounts relative to one another, will provide a apparent digestibility of at least 75%, preferably 80% and most preferably 95%, and which will provide the highest apparent digestibility*(AD) and energy density of any natural food or dietetic composition. The mineral-free, protein-free carbohydrate and highly polyunsaturated vegetable fat composition will provide an exceptional high Energy Density, providing in the liquid form composition at least 4Kcal/cc=3Kcal/g, preferably 4.4 Kcal/cc=3.4-Kcal/g, and high lipids' polyunsaturated/saturated (P/S) ratio, providing a P/S of a least 4.6, preferably 7.0 and most preferably 8.2., compared with any natural food or palatable dietetic composition. The composition may also contain vitamins and/or minerals.

*Heymfield, S.D., Williams, P.J. in "Modern Nutrition In Health and Disease", Shils, M.E., Young, V.R. (Eds), page 819, Lea & Febiger, Philadelphia 1988.

The specific carbohydrate and specific polyunsaturated vegetable fat compositions have particular use in providing energy and Essential Fatty Acids (EFA), for prevention or treatment of Protein-Calorie Malnutrition (PCM). In particular, the composition may be used when further energy and EFA intake is required, and specifically as a complement of amino acid composition intake for supportive nutrition in the case of trauma due to burns, surgery or in disease, such as renal disorders, liver disorders, diabetes mellitus, gout, and the like.

The specific carbohydrate and specific polyunsaturated vegetable fat compositions of the invention may be utilized as a complement, in the prevention and treatment of Protein-Calorie Malnutrition (PCM) as a supplement and/or substitute of carbohydrate and/or fat of the regular diet. In particular, the compositions may be used as a nutritional complement in conditions such as: Protein-Calorie Malnutrition (PCM), cystic fibrosis, anorexia nervosa, immunodeficiency caused by malnutrition, treatment and prevention of malnutrition in AIDS patients, gout, hepatic disorders, burn therapy, renal disorders, alcoholism rehabilitation, tuberculosis, pre and post surgery, hospitalized patients' diet, neurological disorders patients, cancer patients, chronic diseases, illicit-drug rehabilitation, malabsorption, food allergy, diarrhea, diabetes mellitus, nutrition in infants, nutrition in adolescents, nutrition in adults, nutrition in elderly.

The specific carbohydrate and specific polyunsaturated vegetable fat compositions of the invention are of special utility in providing nutritional complement to patients suffering from Acquired Immune Deficiency Syndrome (AIDS) or Aids Related Complex (ARC) in the treatment of Protein-Calorie Malnutrition (PCM), such as kwashiorkor or marasmus and the like.

If desired the specific carbohydrate and specific polyunsaturated vegetable fat compositions of the invention may be used as supplement/replacement compositions for use in providing and/or enhancing a basic source of nutrition for infants, children and adults. It is of particular utility in geriatric patients.

The composition may be given as a solution in water, or as a dispersion in a suitable liquid, or semisolid medium.

The specific protein-free carbohydrate and protein-free polyunsaturated fat are those which provide an apparent digestibility (AD) of at least 75%. Using this parameter of evaluation, it is possible using the compositions and methods of the present invention to obtain at least 90% AD and through the use of preferred embodiments up to 99% AD.

The exceptional high AD and energetic (Energy Density) content, per weight and per volume, are obtained because of the extremely high absorption rates that are possible because of the particular compositions devised by the applicant.

DETAILED DESCRIPTION OF THE INVENTION

The amino acid composition of the invention is based on the use of crystalline amino acids in specific relative amounts which provide an net nitrogen utilization (NNU) of at least 75%. For example, if a particular subject who is fed which an amino acid formula has a nitrogen intake of 100.0 g. and a total nitrogen output of 100.0 g., the NNU of the formula is 100%. If the subject's nitrogen intake is 100 and the output is 128, then the NNU of the formula is 72%.

Using this parameter of evaluation, it is possible using the compositions and methods of the present invention to obtain at least 90% NNU and through the use of preferred embodiments up to 100% NNU.

The exceptionally high NNU are believed to be obtained because of the extremely high absorption rates that are possible because of the particular compositions devised by the applicant.

The amino acid composition of the invention comprise those having the following proportions of amino acids in grams per 10 grams of composition:
(a) from 1.217 to 1.647 isoleucine;
(b) from 1.827 to 2.735 leucine;
(c) from 1.260 to 2.359 lysine;
(d) from 0.232 to 0.778 methionine;
(e) from 0.843 to 1.314 phenylalanine;
(f) from 0.970 to 1.287 threonine;
(g) from 0.208 to 0.467 tryptophan; and
(h) from 1.260 to 1.900 valine.

|  | (I) |
|---|---|
| isoleucine | 1.217–1.530 |
| leucine | 1.827–2.735 |
| lysine | 1.260–2.078 |
| methionine | 0.232–0.778 |
| phenylalanine | 0.934–1.314 |
| threonine | 0.970–1.287 |
| tryptophan | 0.208–0.467 |
| valine | 1.391–1.900 |
|  | (II) |
| isoleucine | 1.251–1.647 |
| leucine | 1.846–2.130 |
| lysine | 2.023–2.359 |
| methionine | 0.490–0.778 |
| phenylalanine | 0.843–1.144 |
| threonine | 1.053–1.287 |
| tryptophan | 0.238–0.401 |
| valine | 1.260–1.426 |
|  | (III) |
| isoleucine | 1.289–1.647 |
| leucine | 1.917–2.130 |
| lysine | 2.023–2.359 |
| methionine | 0.490–0.778 |
| phenylalanine | 0.843–1.144 |

-continued

|  |  |
|---|---|
| threonine | 1.053–1.271 |
| tryptophan | 0.238–0.319 |
| valine | 1.342–1.426 |
| (IV) | |
| isoleucine | 1.251–1.408 |
| leucine | 1.846–2.054 |
| lysine | 2.086–2.359 |
| methionine | 0.621–0.778 |
| phenylalanine | 0.969–1.144 |
| threonine | 1.106–1.287 |
| tryptophan | 0.293–0.401 |
| valine | 1.260–1.422 |
| (V) | |
| isoleucine | 1.372–1.530 |
| leucine | 1.827–2.539 |
| lysine | 1.550–2.078 |
| methionine | 0.490–0.708 |
| phenylalanine | 0.969–1.177 |
| threonine | 0.970–1.157 |
| tryptophan | 0.208–0.373 |
| valine | 1.422–1.600 |
| (VI) | |
| isoleucine | 1.217–1.530 |
| leucine | 1.952–2.735 |
| lysine | 1.260–1.999 |
| methionine | 0.232–0.778 |
| phenylalanine | 0.934–1.314 |
| threonine | 1.043–1.287 |
| tryptophan | 0.266–0.467 |
| valine | 1.391–1.900 |
| (VII) | |
| isoleucine | 1.372–1.445 |
| leucine | 2.192–2.539 |
| lysine | 1.550–1.770 |
| methionine | 0.490–0.642 |
| phenylalanine | 0.969–1.155 |
| threonine | 0.970–1.052 |
| tryptophan | 0.282–0.319 |
| valine | 1.486–1.571 |
| (VIII) | |
| isoleucine | 1.451–1.530 |
| leucine | 1.827–1.846 |
| lysine | 2.020–2.078 |
| methionine | 0.490–0.642 |
| phenylalanine | 0.969–1.144 |
| threonine | 1.115–1.157 |
| tryptophan | 0.368–0.373 |
| valine | 1.422–1.483 |
| (IX) | |
| isoleucine | 1.328–1.357 |
| leucine | 1.917–1.951 |
| lysine | 2.086–2.250 |
| methionine | 0.642–0.673 |
| phenylalanine | 0.969–1.144 |
| threonine | 1.196–1.287 |
| tryptophan | 0.333–0.340 |
| valine | 1.342–1.422 |
| (X) | |
| isoleucine | 1.366–1.408 |
| leucine | 1.846–1.917 |
| lysine | 2.267–2.359 |
| methionine | 0.674–0.778 |
| phenylalanine | 0.969–1.144 |
| threonine | 1.106–1.157 |
| tryptophan | 0.311–0.333 |
| valine | 1.260–1.313 |
| (XI) | |
| isoleucine | 1.289–1.647 |
| leucine | 1.917–2.130 |
| lysine | 2.023–2.359 |
| methionine | 0.622–0.778 |
| phenylalanine | 0.843–0.988 |
| threonine | 1.053–1.271 |
| tryptophan | 0.238–0.298 |
| valine | 1.342–1.426 |
| (XII) | |
| isoleucine | 1.251–1.328 |
| leucine | 1.950–2.067 |
| lysine | 2.078–2.315 |
| methionine | 0.490–0.689 |
| phenylalanine | 0.969–1.144 |
| threonine | 1.106–1.152 |
| tryptophan | 0.282–0.401 |
| valine | 1.306–1.422 |

Preferred compositions include the following proportions by weight of the amino acids:

|  |  |
|---|---|
| (XIII) | |
| isoleucine | 1.217–1.477 |
| leucine | 2.281–2.735 |
| lysine | 1.332–1.999 |
| methionine | 0.232–0.608 |
| phenylalanine | 0.934–1.136 |
| threonine | 1.043–1.287 |
| tryptophan | 0.304–0.467 |
| valine | 1.391–1.900 |
| (XIV) | |
| isoleucine | 1.408–1.530 |
| leucine | 1.952–2.077 |
| lysine | 1.260–1.521 |
| methionine | 0.674–0.778 |
| phenylalanine | 1.257–1.314 |
| threonine | 1.106–1.146 |
| tryptophan | 0.266–0.373 |
| valine | 1.581–1.700 |

The especially preferred compositions include those having the following proportions by weight:

|  | (I) | (II) |
|---|---|---|
| isoleucine | 1.438 | 1.482 |
| leucine | 2.287 | 1.963 |
| lysine | 1.650 | 1.428 |
| methionine | 0.283 | 0.699 |
| phenylalanine | 0.943 | 1.288 |
| threonine | 1.226 | 1.111 |
| tryptophan | 0.448 | 0.368 |
| valine | 1.721 | 1.656 |
|  | (III) | (IV) |
| isoleucine | 1.310 | 1.341 |
| leucine | 2.053 | 1.922 |
| lysine | 2.189 | 2.144 |
| methionine | 0.621 | 0.651 |
| phenylalanine | 1.029 | 1.027 |
| threonine | 1.107 | 1.211 |
| tryptophan | 0.293 | 0.338 |
| valine | 1.390 | 1.358 |
|  | (V) | (VI) |
| isoleucine | 1.381 | 1.311 |
| leucine | 1.891 | 1.951 |
| lysine | 2.297 | 2.266 |
| methionine | 0.682 | 0.752 |
| phenylalanine | 1.029 | 0.959 |
| threonine | 1.113 | 1.119 |
| tryptophan | 0.318 | 0.256 |
| valine | 1.284 | 1.376 |
|  | (VII) | (VIII) |
| isoleucine | 1.443 | 1.484 |
| leucine | 2.226 | 1.832 |
| lysine | 1.760 | 2.064 |
| methionine | 0.556 | 0.580 |
| phenylalanine | 1.100 | 1.067 |
| threonine | 1.041 | 1.136 |
| tryptophan | 0.317 | 0.371 |
| valine | 1.553 | 1.461 |

The compositions of the invention may be utilized in the prevention and/or treatment of nutritional and/or metabolic disorders in healthy or sick people as a supplement and/or substitute to the regular diet. In particular, the compositions may be used for nutrition in conditions such as: Protein-Calorie Malnutrition (PCM), cystic fibrosis, anorexia nervosa, immunodeficiency caused by malnutrition, treatment and prevention of malnutrition in AIDS patients, gout, renal failure, hepatic disorders, burn therapy, hypovitaminosis, hypercholesterolemia, hypoalbuminemia, alcoholism, hemophilia, tuberculosis, pre and post-surgery, hospitalized patients' diet, neurologic disorders patients, pre-menstrual edema and nutritional losses of menstruation, neoplasms, chronic diseases, illicit-drug rehabilitation, malabsorption, food allergy, peptic ulcer, diarrhea, gastrointestinal disorders, short bowel syndrome, hyperlipidemia, diabetes mellitus, gall bladder disorders, nutrition in infants, nutrition in adolescents, nutrition in adults, nutrition in elderly, nutrition in convalesent patients and nutrition during athlete's training.

The amino acid composition of the invention is of special utility in providing nutrition to patients suffering from Acquired Immune Deficiency Syndrome (AIDS) or Aids Related Complex (ARC). The composition of the invention may also be used in the treatment of Protein-Calorie Malnutrition (PCM), such as kwashiorkor, marasmus and the like.

If desired, the amino acid composition of the invention may be used to the treatment and prevention of obesity, or as a supplement/replacement composition for use in providing and/or enhancing a basic source of nutrition for infants, children and adults. It is of particular utility in geriatric patients.

In the treatment and prevention of obesity, as well as in the maintenance of optimal body weight it may be desirable to include decreasing amounts of a source of calories to avoid hypoglycemia. For example, in the first day may include 2000 Kcal and this may be decreased by 200 Kcal for each day to a minimum of 800 K/cal/day. For physician supervised diets in an institution, a diet without any substantial source of calories may be used after gradually decreasing amounts of a source of calories are used. The calorie content may be reduced to less than 100 Kcal may be used, if necessary.

It is possible to substitute cysteine for part of the methionine component; and to substitute tyrosine for part of the phenylalanine component.

The amino acid compositions of the invention have particular use in pregnancy because the proper requirement of protein is supplied without increasing Blood Urea Nitrogen (BUN) or other nitrogen metabolic residuals; in addition, its use prevents nutritional and metabolic disorders and their consequences during pregnancy and lactation.

The amount of the amino acid composition to be used in each particular condition may generally be determined by titration of individual patients to obtain the desired nutritional response or by use of from 0.5 g to 5.0 g/kg of ideal body weight/per day of the amino acid composition of the invention, and preferably from 1.0 g to 2.0 g/kg of body ideal weight/per day given orally or parenteraly. Certain of the compositions of the invention may be used intravenously, however, the preferred route of administration is orally via normal feeding or by a stomach tube because absorption is higher and the nosocomial infections associated with intravenous feeding may be avoided. The amino acid composition may be administered dry as a powder, in capsules or tablets, as a solution or dispersion in a suitable liquid, or in a semi-solid medium. The ideal weight is determined according to the method set forth in Example I.

The mineral-free, protein-free carbohydrate and highly polyunsaturated vegetable fat composition of the invention is based on the use of specific mineral-free, protein-free carbohydrate(s) and mineral-free, protein-free highly polyunsaturated vegetable fat(s), which will provide an exceptional high AD, providing an apparent digestibility of at least 75%, preferably 80% and most preferably 95%.

The use of mineral-free, protein-free carbohydrate(s) is in the form of the alcohol of glucose, namely sorbitol (glucitol), and/or disaccharides, namely sucrose, and/or maltose. Sorbitol has a therapeutic value as a replacement carbohydrate in the diet of diabetics; sucrose is perhaps the most common and best known disaccharide in the diet, and maltose, which has a relative sweetness value of 40, can replace all or part of the sucrose contents to decrease the sweetness of the composition, and make it more palatable.

The use of mineral-free, protein-free vegetable fat is in the form of vegetable oils with a polyunsaturated/saturated ratio (P/S ratio) of a least 4.6, preferably 7.0 and most preferably 8.2. The use of vegetable oils with a very high (more than 4.5 P/S ratio), namely safflower oil (8.2 P/S ratio, and/or sunflower oil (7.0 P/S ratio), and/or corn oil (4.6 P/S ratio)(5), is because has been demonstrated convincingly that diets enriched in EFA such as linoleic acid (highly present in safflower oil and/or sunflower oil and/or corn oil) and reduced in saturated fatty acids do lower significantly LDL and VLDL cholesterol in man at both 30 and 40 in % of fat levels.

It is to be understood that one or more of the mineral-free, protein-free carbohydrates may be used with one or more of the highly polyunsaturated vegetable fats to provide a composition having the desired flavor and calorie content. Distilled water or any other suitable mineral-free diluent may be added, as desired.

The exceptional high AD of the nutritional composition of the invention, providing a carbohydrate and vegetable fat composition with an exceptional high apparent digestibility (AD), providing at least 75%, preferably 80% and most preferably 95% AD, and an exceptional high Energy density, providing in the liquid form composition at least 4Kcal/cc (3Kcal/g), preferably 4.4 Kcal/cc (3.4 Kcal/g), and most preferably 4.7 Kcal/cc (3.7 Kcal/g), and an exceptional vegetable fat P/S ratio, providing a P/S of at least 4.6, preferably 7.0 and most preferably 8.2 are obtained by the use of the applicants' compositions.

| Formula I | |
|---|---|
| Maltose | 70-95 wt. % |
| Safflower Oil | 5-30 wt. % |
| TOTAL | 100.0 wt. % |
| Formula II | |
| Maltose | 70-95 wt. % |
| Safflower Oil and Sunflower Oil | 5-30 wt. % |
| TOTAL | 100.0 wt. % |

(The safflower oil and sunflower oil may comprise from 1-99 wt. % to 99-1 wt. % of the total oil content)

| Formula III | |
|---|---|
| Sorbitol | 70-95 wt. % |
| Safflower Oil | 5-30 wt. % |
| TOTAL | 100.0 wt. % |
| Formula IV | |
| Sorbitol | 70-95 wt. % |
| Safflower Oil and | 5-30 wt. % |

-continued

| | | |
|---|---|---|
| Sunflower Oil | | |
| TOTAL | 100.0 wt. % | |

(The safflower oil and sunflower oil may comprise from 1-99 wt. % to 99-1 wt. % of the total oil content)

Formula V

| | | |
|---|---|---|
| Sucrose and Maltose | 70-95 | wt. % |
| Corn Oil | 5-30 | wt. % |
| TOTAL | 100.0 | wt. % |

Formula VI

| | | |
|---|---|---|
| Sucrose and Maltose | 70-95 | wt. % |
| Sunflower Oil | 5-30 | wt. % |
| TOTAL | 100.0 | wt. % |

Formula VII

| | | |
|---|---|---|
| Sorbitol and Maltose | 70-95 | wt. % |
| Safflower Oil | 5-30 | wt. % |
| TOTAL | 100.0 | wt. % |

Formula VIII

| | | |
|---|---|---|
| Sorbitol and Maltose | 70-95 | wt. % |
| Safflower Oil and Sunflower Oil | 5-30 | wt. % |
| TOTAL | 100.0 | wt. % |

(The safflower oil and sunflower oil may comprise from 1-99 wt. % to 99-1 wt. % of the total oil content)

Formula IX

| | | |
|---|---|---|
| Sucrose, Maltose and Sorbitol | 70-95 | wt. % |
| Safflower Oil, Sunflower Oil and Corn Oil | 5-30 | wt. % |
| TOTAL | 100.0 | wt. % |

(The safflower oil, sunflower oil and corn oil may comprise from 1-99 wt. % to 99-1 wt. % of the total oil content)

Formula X

| | | |
|---|---|---|
| Sucrose, Maltose and Sorbitol | 70-95 | wt. % |
| Corn Oil | 5-30 | wt. % |
| TOTAL | 100.0 | wt. % |

Vitamins are organic micronutrients essential for normal growth and maintenance of life. Vitamins cannot be synthesized by the organism and for these reasons they have to be supplied from an exogenous source. Vitamins provide the only source of certain coenzymes necessary for metabolism, the biochemical process that supports life. Vitamins are classified as fat-soluble and water-soluble. Fat-soluble vitamins, namely A, D, E, and K are stored in body fat and may therefore accumulate in quantities that can be toxic. The B vitamins and vitamin C are water-soluble and most of them are rapidly excreted in the urine and thus rarely cause toxicity. Vitamin C and B12 tend to be stored in the body.

Effects of vitamin(s) deficiency, as well as, toxicity (excessive intake) are dangerous to health, and must be avoided.

The inorganic nutritional minerals and trace elements present in food are essential for health. Some such as calcium, phosphorus, and potassium, occur in the body in concentrations 0.005%. Others termed "trace elements" such as iron, zinc, and iodine, occur in much smaller concentrations (0.005%).

The inorganic elements have many functions such as electrolytes, components of the bones and teeth, components of the prosthetic group of enzymes, and others.

Effects of mineral(s) deficiency, as well as, toxicity (excessive intake) are dangerous for health and must be avoided.

The preferred group of vitamins and minerals are set forth below. It should be understood that variations in the preferred group may be made but the essence of the applicant's inventive use of vitamins and minerals in the administration of these nutritional elements is in the use of a specific ratio of vitamins and minerals to the total amount of specific amino acids administered to a particular patient taking into consideration the interrelationship specific amino acid(s), vitamin(s) and mineral(s). This is to allow high NNU, as well as, to avoid hypo or hypervitaminnosis (deficiency or toxicity).

| | | |
|---|---|---|
| Sodium | 13.00-23.00 | mg |
| Potassium | 41.00-69.00 | mg |
| Magnesium | 2.50-5.00 | mg |
| Calcium | 27.00-45.00 | mg |
| Manganese | 1.50-3.50 | mcg |
| Iron | 37.00-100.00 | mcg |
| Cobalt | 1.00-2.00 | mcg |
| Copper | 35.00-65.00 | mcg |
| Zinc | 0.16-0.28 | mg |
| Nickel | 0.75-2.50 | mcg |
| Chromium | 50.00-85.00 | mcg |
| Molybdenum | 0.70-5.00 | mcg |
| Vanadium | 0.35-0.65 | mcg |
| Phosphorus | 11.00-35.00 | mg |
| Chloride | 30.00-50.00 | mg |
| Fluoride | 13.00-22.00 | mcg |
| Iodine | 4.00-8.00 | mcg |
| Selenium | 2.00-4.50 | mcg |
| Bromine | 0.07-0.13 | mg |
| Boron | 4.00-8.00 | mcg |
| Silicon | 22.00-40.00 | mg |
| Vitamin A | 60.02-109.00 | mcg |
| Vitamin D | 37.00-63.00 | ng |
| Alpha-Tocopherol | 0.78-1.30 | ng |
| Vitamin K | 2.00-4.00 | mcg |
| Vitamin B1 | 10.00-20.00 | mcg |
| Vitamin B2 | 27.00-48.00 | mcg |
| Nicotinamide | 0.13-0.23 | mg |
| Pantotenic Acid | 0.18-0.18 | mcg |
| Vitamin B6 | 13.00-23.00 | mcg |
| Biotin | 0.43-0.73 | mcg |
| Folic Acid | 3.50-6.50 | mcg |
| Vitamin B12 | 35.00-65.00 | ng |
| Vitamin C | 3.00-6.50 | mg |

The compositions of the invention may be given as dry as a powder, or as tablets, or as a solution in water, or as a dispersion in a suitable liquid, or semi-solid medium. The mineral-free, protein-free carbohydrate and highly polyunsaturated vegetable oil compositions of the invention may be utilized as a complement in the prevention and treatment of Protein-Calorie Malnutrition (PCM) or as a supplement and/or substitute of carbohydrate and/or fat of the regular diet. In particular, these compositions may be used for nutritional complement in conditions such as: Protein Calorie Malnutrition (PCM), cystic fibrosis, anorexia nervosa, immunodeficiency caused by malnutrition, treatment and prevention of malnutrition in AIDS patients, hypercholesterolemia, gout, hepatic disorders, burn therapy, renal disorders, alcoholism rehabilitation, tuberculosis, pre and post surgery, hospitalized patients' diet, neurological disorders, cancer patients, chronic diseases, illicit-drug rehabilitation, malabsorption, food allergy, diarrhea, diabetes mellitus, nutrition in infants, nutrition in adolescents, nutrition in adults, nutrition in elderly.

These compositions of the invention are of special utility in providing a nutritional complement to patients suffering from Acquired Immune Deficiency Syndrome (AIDS) or Aids Related Complex (ARC).

The composition of the invention may also be used as a complement in the treatment of Protein-Calorie Malnutrition (PCM), such as kwashiorkor or marasmus and the like.

If desired, the composition of the invention may be used as a supplement/replacement composition for use in providing and/or enhancing a basic source of nutrition for infants, children and adults. It is of particular utility in geriatric patients.

The amount of the composition to be used in each particular condition may generally be determined in accordance of the energetic need of individual patients to obtain that desired nutritional response. The preferred route is the oral route, but a tube may be used for direct infusion into the alimentary tract.

When patients are treated with compositions according to this invention, it is desirable to initially administer 10% of the total calculated dose and to increase the dose by 10% per day over a 10 day period. This is done to avoid gastrointestinal problems such as bloating and diarrhea.

The composition may be given as a solution in water, or as a dispersion in a suitable liquid, or semisolid medium.

It is to be understood that convention sources of dietary fiber may be taken in combination with the compositions of the invention, if desired. These sources include fruits, psyllium, bran, vegetables, etc.

EXAMPLE 1

A comparative double-blind, triple cross-over study was carried out in sixty-six subjects, during a 114 day period, to examine subject's nitrogen balances to determine the net nitrogen utilization (NNU) of consumed protein or amino acid formula, during Diets A, B and C.

A group of 66 patients were fed with a Metabolism Equalizing and Stabilizing Diet (MESD) for a 30 day period. The composition of the formula in grams per 10 grams of amino acids was:

TABLE I

| | |
|---|---|
| Ile | 1.438 |
| Leu | 2.281 |
| Lys | 1.650 |
| Met | 0.283 |
| Phe | 0.943 |
| Thr | 1.226 |
| Trp | 0.448 |
| Val | 1.721 |

Sixty-six healthy subjects were fed with MESD, during the 30 day period, in the preliminary phase of this study, with the purpose of equalizing and stabilizing their protein and energy metabolisms, thus avoiding different metabolism degrees, which could affect their nitrogen balances.

To avoid common errors in energy intake, which also could affect nitrogen balance, MESD supplied a constant energy intake per subject equivalent to 50 Kcal/Kg/day, during the 30 day period.

To avoid common errors in nitrogen intake, which could affect the nitrogen balance, the carbohydrate and fat of MESD were selected from the essentially protein-free foods of Table IA.

TABLE IA

| Food | Composition × 100 g Protein | Energy (Calories) |
|---|---|---|
| Fruits: | | |
| Apricot | 0.8 | 57 |
| Pineapple | 0.4 | 52 |
| Peach | 0.8 | 52 |
| Strawberry | 0.8 | 36 |
| Pondapple | 0.4 | 52 |
| Tangerine | 0.7 | 43 |
| Mango | 0.5 | 59 |
| Apple | 0.3 | 58 |
| Muskmelon | 0.5 | 25 |
| Orange | 0.7 | 50 |
| Loquat | 0.2 | 44 |
| Papaya | 0.5 | 32 |
| Pear | 0.3 | 56 |
| Watermelon | 0.5 | 22 |
| Vegetables: | | |
| Celery | 0.8 | 19 |
| Eggplant | 1.0 | 27 |
| Waxgourd | 0.5 | 14 |
| Chayote | 0.9 | 31 |
| Lettuce | 1.0 | 13 |
| Cucumber | 0.7 | 15 |
| Ripe tomato | 0.8 | 21 |
| Sweet Cassava | 1.0 | 132 |
| Carrot | 0.8 | 41 |
| Sucrose | 0.0 | 384 |
| Corn oil | 0.0 | 384 |
| Maltose | 0.0 | 384 |
| Sorbitol | 0.0 | 384 |
| Sufflower Oil | 0.0 | 884 |
| Sunflower Oil | 0.0 | 884 |
| Corn Oil | 0.0 | 844 |

To avoid unnecessary nitrogen loss, and to stabilize subjects' protein metabolisms, MESD also supplied a decreasing amount of protein from the amino acid formula (Table I) during the 30 day period as follows:

(a) 1st and 2nd day:protein intake of 0.80 g/Kg/day;
(b) 3rd and 4th day:protein intake of 0.75 g/Kg/day;
(c) 5th and 6th day:protein intake of 0.70 g/Kg/day;
(d) 7th and 8th day:protein intake of 0.65 g/Kg/day;
(e) 9th and 10th day:protein intake of 0.60 g/Kg/day;
(f) 11th and 12th day:protein intake of 0.55 g/Kg/day;
(g) 13th and 14th day:protein intake of 0.50 g/Kg/day;
(h) 15th and 16th day:protein intake of 0.45 g/Kg/day; and
(i) from the 17th to the 30th day: protein intake of 0.40 g/Kg/day.

The protein requirement was calculated for each subject in accordance with each subjects ideal weight. The amino acid formula was fed in three divided doses at 8:00 a.m.; 2:00 p.m. and 8:00 p.m. A vitamin-mineral supplement according to Example 4 was also fed to each patient.

After the MESD conclusion, at the beginning of the main phase, the sixty-six healthy subjects were randomly divided into three matched groups, according to sex and number, and named Groups 1, 2 and 3. In accordance with the diet sequence (Table II), the main phase of this study, was conducted during three consecutive 28 day periods, with the purpose of examining subjects' nitrogen balances, in order to evaluate their net nitrogen utilization (NNU) of consumed protein and amino acid formulas, during the periods of Diets A, B and C.

TABLE II

| Sequence of the Diets by Group | | | | |
|---|---|---|---|---|
| Group 1 | MESD | A | B | C |
| Group 2 | MESD | B | C | A |
| Group 3 | MESD | C | A | B |

To achieve this purpose, Groups 1, 2 and 3, each comprised of twenty-two healthy subjects, were fed with diets A, B, and C, following the obligatory sequence (Table II) and schedule (Table III).

TABLE III

| Sequence of Diets by Group and Period | | | |
|---|---|---|---|
|  | Group I | Group 2 | Group 3 |
| First Period (28 days) Diet | A | B | C |
| Second Period (28 days) Diet | B | C | A |
| Third Period (28 days) Diet | C | A | B |

Diets A, B, and C consisted of an identical composition of protein, carbohydrate, fat, vitamins and minerals, but of a different protein source. The diets had the following characteristics:

DIET "A" provided to the subject, a protein intake of 0.4 g/Kg/day, equivalent to 64 mg/Kg/day of nitrogen, from the amino acid formula of Table I and an energy intake of 50 Kcal/Kg/day, from protein-free carbohydrate and fat from Table IA.

DIET "B" provided to the subject a protein intake of 0.4 g/Kg/day, equivalent to 64 mg/Kg/day of nitrogen, from hen whole egg amino acid formula (Table IV) and an energy intake of 50 Kcal/Kg/day, from protein-free carbohydrate and fat from Table IA.

TABLE IV

| Amino Acid Composition of Hen Whole Egg* (Grams of amino acids in 100 g of protein) | |
|---|---|
| Arg | 1.04 |
| Asp | 7.75 |
| Cys—Cys | 2.58 |
| Glu | 13.69 |
| Gly | 3.91 |
| His | 2.65 |
| Ile | 7.35 |
| Leu | 9.73 |
| Lys | 7.08 |
| Met | 3.46 |
| Phe | 6.39 |
| Pro | 4.69 |
| Ser | 9.29 |
| Thr | 5.50 |
| Trp | 1.82 |
| Tyr | 4.76 |
| Val | 8.21 |

Corn Oil and sucrose were added to the previous composition, in the following amounts, to provide an energy content in that form of fat and carbohydrate content that approximates that of dried hen whole egg.*
*Based on the data presented in Orr, M. D., and Watt, B. K., "Amino Acid Content of Foods" U.S. Dept. Agr. 1957.

| Corn oil | 90.00 g |
|---|---|
| Sucrose | 7.00 g |

The achievement of the equalization among formula compositions was obtained by adding to both Diet A - formula of Table I, and Diet B - hen whole egg amino acids formula of Table IV the amount of 0.9 g of fat (corn oil), plus 0.07 g of carbohydrate (sucrose) per each gram of protein content of the formulas, achieving an equivalent composition of protein, fat and carbohydrate as contained in the Diet C—dried hen whole egg as follows:

Dried Hen Whole Egg Composition in 100g.*
* INCAP-ICNND Composition of Foods, 1961.

| Protein | 47.0 g |
|---|---|
| Fat | 41.2 g |
| Carbohydrate | 3.4 g |
| Kcal. | 584 |

DIET "C" provided to the subject a protein intake of 0.4 g/Kg/day, equivalent to 64 mg/Kg/day of nitrogen, from dried hen whole egg and an energy intake of 50 Kcal/Kg/day from protein-free carbohydrate and fat (Table IA).

To avoid common errors in determining nitrogen intake, which could affect the nitrogen balance, the carbohydrate and fat of Diets A, B and C were substantially protein-free (Table IA).

To avoid common errors in determining energy intake, which could also affect nitrogen balance, Diets A, B and C supplied a constant energy intake per subject equivalent to 50 Kcal/Kg/day, during each 28 day period.

To avoid over-estimating nitrogen intake, caused by unconsumed daily protein or amino acids formula during each day period, all sixty-six subjects were fed three times per day (8:00 a.m.; 2:00 p.m.; and 8:00 p.m.) achieving the total consumption of their allotted formula.

To avoid error in determining energy intake, which could affect nitrogen balance, formulas given during Diets A, B and C had an equivalent composition of protein, fat and carbohydrate, which provided the same energy intake.

The identification by the subject of his/her formula by its flavor which could affect the double-blind characteristic of the sutdy was prevented by adding to the formulas of Diets A, B and C a common fruit shake. To avoid errors in energy intake, this fruit shake, by itself, provided the same energy intake. The fruit for the shake was changed almost daily, and was chosen from Table V.

TABLE V

| Food Fruits | Composition × 100 g Protein | Energy (Calories) |
|---|---|---|
| Pineapple | 0.4 | 52 |
| Pondapple | 0.4 | 52 |
| Papaya | 0.5 | 32 |
| Watermelon | 0.5 | 22 |

To avoid a nitrogen over-intake per g/kg/day, which could affect the nitrogen balance, the subject's protein requirement was based on his/her ideal weight. A daily vitamin-mineral supplement according to Example 4 was given to all subjects.

Determining Weight

The subject's weight (in kg) was determined, in the early morning after subject's urination and evacuation, and before breakfast. The result was rounded off to the nearest 0.100 kg (range 50 g).

Determining Ideal Weight

The subject's ideal weight (in kg) was obtained by subtracting factor 100 from the subject's height (in cm), then multiplying the result by either factor 0.9 (male) or 0.8 (female), in accordance with subject's sex. The result was rounded off to the nearest 0.500 kg (range 250 g). The following formula was applied:

male's ideal weight = [(Height − 100) × 0.9] kg female's ideal weight = [(Height − 100 × 0.8] kg

Determining Nitrogen Balance

To determine the subject's nitrogen balance, the following formula was used:

$B = I − (U + F + S)$ where:
B = N balance;
I = N intake;
U = N loss in urine;
F = N loss in feces; and
S = N dermal losses.

The nitrogen balance represents the difference between N intake (I), and N output (U + F + S), the difference being either positive (N retention), as in active growth, negative (N loss), or zero (N equilibrium).

Determining Nitrogen Intake

To determine the subject's nitrogen intake (I), the following formula is used:

Diet protein amount = Dietary nitrogen × 6.25 where use of factor 6.25, implies that the average protein contains 16% nitrogen.

Determining Nitrogen Loss

The urine (U) and feces (F), of each subject are collected throughout each 24-hour day of each consecutive 28 day period, to determine the nitrogen loss by micro-Kjeldahl techniques.

To determine the subject's nitrogen dermal and minor route losses (S), a constant factor was used:

(S) = 5 mg × subject weight (kg) × day

Determining Nitrogen Balance

This calculation was made by taking into consideration the subject's real weight. To avoid any misinterpretation in the subject's daily nitrogen balance, which is not usually constant, the subject's diet nitrogen intake (I) per period, and the diet nitrogen output (U + F + S) per period, were obtained by adding up the subject daily nitrogen intake and output amounts, during the diet period.

The subject's nitrogen balance was obtained by the difference between the dietary nitrogen intake (I) per period, and the dietary nitrogen output (U + F + S) per period.

Determining Mean Nitrogen Loss

The mean of each subject's nitrogen loss, per period, was obtained by adding up each subject nitrogen loss amount during a diet period, and dividing the result by the total number of subjects.

Determining Mean Protein Loss

The mean protein loss per each subject per period, is obtained by multiplying the mean nitrogen loss per period by factor 6.25. All calculations were in accordance with the following formula:

PROTEIN = (N g) × 6.25 where it is assumed that the N content of the mixed proteins of the body is 16%. Thus 1 g of N excreted represent a loss from the body of 6.25 g of mixed proteins.

Determining Mean Tissue Loss

The mean tissue loss per subject per period, is obtained by multiplying the mean protein loss per period by factor 5. All calculations are in accordance with the following formula:

LEAN TISSUE = (N g) × 6.25 × 5

To illustrate: the N content of the mixed proteins of the body is 16%. Thus 1 g of N excreted represents a loss from the body of 6.25 g of mixed proteins. Intracellular protein exists in approximately a 20 to 25% aqueous solution in the lean tissue of the body (the fat-free, connective tissue-free, and bone-free "wet" tissue).

Assuming that 1 g protein is associated with 5 g of hydrated lean tissue, then 1 g of excreted nitrogen represents a loss of 1 × 6.25 × 5 = 31.25 g of lean tissue.

Determining Mean Nitrogen Loss Per Kilo Per Period

The subjects' mean nitrogen loss per subject per kg per period, is obtained by dividing the subjects' mean nitrogen loss per period by the mean ideal weight.

Determining Range of Mean Nitrogen Loss Per Kilo Per Period

The subjects' range of mean nitrogen loss per subject per kg per period, is obtained by calculating the difference between the highest and lowest subject's nitrogen loss per period.

| RESULTS OF THE STUDY GROUP "1" NITROGEN BALANCE RESULTS BY DIET | | | |
|---|---|---|---|
| Diet | A | B | C |
| Group 1 | equilibrium | negative | negative |

The following are the nitrogen balance results obtained from Group "1" comprised of twenty-two subjects, with a mean ideal weight of 55 kg, during each 28 day diet period:

| Period: 28 days | Subjects: 22 |
|---|---|
| DURING DIET "A" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |
| DURING DIET "B" | |
| NITROGEN BALANCE per subject per period: | NEGATIVE* |
| Mean Nitrogen Loss per subject per period: | 28.56 g |
| Mean Nitrogen Loss per kg per period: | 519 mg |
| Mean Protein Loss per subject per period: | 178.50 g |
| Mean Lean Tissue Loss per subject per period: | 892.50 g |

-continued

| Period: 28 days | Subjects: 22 |
|---|---|
| DURING DIET "C" | |
| NITROGEN BALANCE per subject per period: | NEGATIVE* |
| Mean Nitrogen Loss per subject per period: | 32.78 g |
| Mean Nitrogen Loss per kg per period: | 596 mg |
| Mean Protein loss per subject per period: | 204.87 g |
| Mean Lean Tissue Loss per subject per priod: | 1,024.37 g |

*found in all twenty two subjects.

| GROUP "2" NITROGEN BALANCE BY DIET | | | |
|---|---|---|---|
| Diet | B | C | A |
| Group 2 | negative | negative | equilibrium |

The following are the nitrogen balance results obtained from Group "2" comprises of twenty-two subjects, with means ideal weight of 53.5 kg, during each 28 day diet period:

| Period: 28 days | Subjects: 22 |
|---|---|
| DURING DIET "B" | |
| NITROGEN BALANCE per subject per period: | NEGATIVE* |
| Mean Nitrogen Loss per subject per period: | 26.51 g |
| Mean Nitrogen Loss per kg per period: | 495 mg |
| Mean Protein Loss per subject per period: | 165.68 g |
| Mean Lean Tissue Loss per subject per period: | 828.43 g |
| DURING DIET "C" | |
| NITROGEN BALANCE per subject per period: | NEGATIVE* |
| Mean Nitrogen Loss per subject per period: | 30.47 g |
| Mean Nitrogen Loss per kg per period: | 569 mg |
| Mean Protein Loss per subject per period: | 190.43 g |
| Mean Lean Tissue Loss per subject per period: | 952.18 g |
| DURING DIET "A" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per priod: | NONE |

*found in all twenty-two subjects.

| GROUP "3" NITROGEN BALANCE BY DIET | | | |
|---|---|---|---|
| Diet | C | A | B |
| Group 3 | negative | equilibrium | negative |

The following are the nitrogen balance results obtained from Group "3" comprises of twenty-two subjects, with a mean ideal weight of 53 kg, during each 28 day diet period:

| Period: 28 days | Subjects: 22 |
|---|---|
| DURING DIET "C" | |
| NITROGEN BALANCE per subject per period: | NEGATIVE* |
| Mean Nitrogen Loss per subject period: | 30.43 g |
| Mean Nitrogen Loss per kg per period: | 574 mg |
| Mean Protein Loss per subject per period: | 190.18 g |
| Mean Lean Tissue Loss per subject per period: | 950.93 g |
| DURING DIET "A" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |
| DURING DIET "B" | |
| NITROGEN BALANCE per subject per period: | NEGATIVE* |
| Mean Nitrogen Loss per subject per period: | 26.57 g |
| Mean Nitrogen Loss per kg per period: | 501 mg |
| Mean Protein Loss per subject per period: | 166.06 g |
| Mean Lean Tissue Loss per subject per period: | 830.31 g |

*found in all twenty-two subjects.

| NITROGEN BALANCE BY GROUP AND DIET | | | |
|---|---|---|---|
| Diet | A | B | C |
| Group 1 | equilibrium | negative | negative |
| Group 2 | equilibrium | negative | negative |
| Group 3 | equilibrium | negative | negative |

The following are the nitrogen balance results obtained from the sixty-six subjects belonging to Groups 1, 2, and 3, with a mean ideal weight of 54 kg, during each consecutives 28 day diet period:

| Period: 28 days | Subjects: 66 |
|---|---|
| DURING DIET "A" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |
| DURING DIET "B" | |
| NITROGEN BALANCE per subject per period: | NEGATIVE* |
| Mean Nitrogen Loss per subject per period: | 27.21 g |
| Mean Nitrogen Loss per kg per period: | 504 mg |
| Range of Mean Nitrogen Loss per kg per period: | 27 mg |
| Mean Protein Loss per subject per period: | 170.06 g |
| Mean Lean Tissue Loss per subject per period: | 850.31 g |
| DURING DIET "C" | |
| NITROGEN BALANCE per subject per period: | NEGATIVE* |
| Mean Nitrogen Loss per subject per period: | 31.22 g |
| Mean Nitrogen Loss per kg per period: | 578 mg |
| Range of Mean Nitrogen Loss per kg per period: | 28 mg |
| Mean Protein Loss per subject per period: | 195.12 g |
| Mean Lean Tissue Loss per subject per period: | 975.62 g |

*found in all sixty-six subjects.

The sixty-six subjects have shown:

(a) the highest net nitrogen utilization (NNU) when receiving the formula of Table I, during Diet A periods, by achieving "equilibrium" in their nitrogen balances;

(b) a lower net nitrogen utilization (NNU) when receiving hen whole egg amino acids formula, during Diet B periods, by obtaining negative nitrogen balances, with a mean nitrogen loss per subject equivalent to 504 mg/kg/period, which was 28% less net nitrogen utilization (NNU) than when receiving the formula of Table I during Diet A; and (c) the lowest net nitrogen utilization (NNU) when receiving dried hen whole egg, during Diet C periods, by obtaining negative nitrogen balances, with a mean nitrogen loss per subject equivalent to 578 mg/kg/period, which was 32% less apparent protein digestibility than when receiving the formula of Table I during Diet A periods.

The hen whole egg protein has been considered to be the protein food with the highest net nitrogen utilization (NNU). The formula of Table I has shown the highest net nitrogen utilization (NNU) by all sixty-six subjects, than both hen whole egg and hen whole egg amino acid formula. It can be concluded that the formula of Table I has a higher apparent protein digestibility than hen whole egg protein.

EXAMPLE 2

This example illustrates the use of the composition of the invention in the treatment of obesity.

A comparative, double-blind, triple cross-over study was carried out in seventy-two subjects, over a 114 day period to examine subjects' nitrogen balances and weight losses during a 28 day period on Diets D (water diet); E (casein amino acid formula) and F (diet of Table 1, Example 1) to determine the net nitrogen utilization (NNU) of consumed amino acid formula, during Diets E and F, as well subjects total loss of weight, loss of lean tissue and fat tissue, during Diets D, E and F.

In the first 30 days of the study, the MESD diet of Example 1 was fed to the patients. During the main phase, the seventy-two healthy subjects were randomly chosen for assignment to three matched groups to evaluate Diets D, E and F with regard to the NNU and total weight loss, loss of lean tissue and loss of fat tissue. The groups contained seventy-two healthy subjects; thirty-six males and thirty-six females.

Group "1" comprised twenty-four healthy subjects, twelve males and twelve females, with a mean weight of 84.100 kg, aged from 21 and 38 years (mean age 28), who were randomly chosen.

Group "2" comprised twenty-four healthy subjects, twelve males and twelve females, with a mean weight of 02.200 kg, aged from 23 to 44 years (mean age 29), who were randomly chosen.

Group "3" comprised twenty-four healthy subjects, twelve males and twelve females, with a mean weight of 76.300 kg, aged from 23 to 41 years (mean age 31), who were randomly chosen.

The following criteria was used for subject selection:
(a) the subject must be in good health;
(b) the subject must weigh more than 15 kg than their ideal weight; and
(c) the subject could not be pregnant.

The following criteria was used to exclude a subject during the study:
(a) the subject who became sick, thus altering his/her nitrogen balance;
(b) the subject who expressed his/her desire not to continue in this study;
(c) the subject who did not follow the prescribed rules of the study; and
(d) the subject who became pregnant.

The seventy-two healthy subjects were initially fed with the MESD diet during a 30 day period in accordance with Example 1.

Diets D, E and F consisted of an identical composition of carbohydrate, fat, vitamins and minerals, but of a different protein amount or source and had the following characteristics:

DIET "D" provided to the subject, a protein intake of 0.0 g/Kg/day, equivalent to 0.0 mg/Kg/day of nitrogen, 0.4g/Kg/day of lactose as a placebo and an energy intake of 12 Kcal/Kg/day, from protein-free carbohydrate and fat of Table IA.

DIET "E" provided to the subject, a protein intake of 0.4 g/Kg/day, equivalent to 64 mg/Kg/day of nitrogen, from casein having amino acid formula having the composition of Table VI, and an energy intake of 12 Kcal/Kg/day, from carbohydrate and fat from Table IA.

TABLE VI

Amino Acids in 100 g of Bovine Casein
(Grams of Amino Acid in 100 g)

| Amino Acid | Grams |
|---|---|
| Ala | 3.8 |
| Arg | 4.3 |
| Asp | 8.4 |
| Cys—Cys | 0.4 |
| Glu | 22.5 |
| Gly | 2.3 |
| His | 2.9 |
| Ile | 6.4 |
| Leu | 7.9 |
| Lys | 8.9 |
| Met | 2.5 |
| Phe | 4.6 |
| Pro | 7.6 |
| Ser | 6.3 |
| Thr | 4.9 |
| Trp | 1.6 |
| Tyr | 8.1 |
| Val | 6.3 |

This table is based on Orr et al., Amino Acid Content of Foods, USDA (1957) and the total value are more than 100 because the hydrolysis of protein results in the addition of water molecules.

Diet "F" provided o the subject, a protein intake of 0.4 g/Kg/day, equivalent to 64 mg/Kg/day of nitrogen, from the amino acid formula of Table I, and an energy intake of 12 Kcal/Kg/day, from protein-free carbohydrate and fat from Table IA.

To avoid common errors in determining nitrogen intake, which could affect the nitrogen balance, the carbohydrate and fat of Diets D, E and F, were substantially protein-free.

To avoid common errors in determining energy intake, which could also effect nitrogen balance, Diets D, E, and F, supplied a constant energy intake per subject equivalent to 12 Kcal/Kg/day, during each 28 day period.

To avoid over-estimating nitrogen intake, caused by unconsumed daily protein or amino acids formulas, during each 28 day period, all seventy-two subjects were fed three times daily at 8:00 a.m.; 2:00 p.m.; and 8:00 p.m. achieving the total consumption of their allotted formula.

To avoid errors in determining energy intake, which could affect nitrogen balance, formulas given during Diets E and F, had an equivalent composition of protein, with the same energy intake.

To avoid affecting the double-blind characteristic of this study, during Diet D (protein-free) periods, a placebo formula, consisting of lactose, was given in the same dosage of 0.4 g/Kg/day as the formulas of Diets E and F.

To avoid the identification by the subject of his/her formula by its flavor, which could affect the double-blind characteristic of this study, the formulas of Diets D, E and F were mixed with a common fruit shake. To avoid errors in energy intake, this fruit shake, by itself, changed almost daily, and was chosen from Table II.

To avoid a subject's energy over-intake which could increase his/her current overweight, the subject's energy requirement was calculated in accordance with his/her ideal weight.

To avoid a nitrogen over-intake per g/Kg/day, which could affect the nitrogen balance, the subject's protein requirement was calculated in accordance with his/her ideal weight.

A daily vitamin and mineral supplement was given to all seventy-two subjects, during the 84 day period, in accordance with the US Recommended Daily Allowance.

Determining Mean Nitrogen Loss

The mean of each subject's nitrogen loss, per period, was obtained by adding up each subject's nitrogen loss amount during a diet period, and dividing the result by the total number of subjects.

Determining Mean Fat Loss

The mean fat loss (in kg), for each subject, per period, was obtained by subtracting from subjects' mean total weight loss the subjects+ mean lean tissue loss. The following formula was applied:

Total Weight Loss=Lean Tissue Loss+Fat Loss

Determining Mean Total Weight Loss Per Kilo Per Period

The mean total weight loss per kg of subject, per period, was obtained by dividing the subjects' mean total weight loss per period by their mean weight per period.

Determining Range of Mean Total Weight Loss Per Kilo Per Period

The range of mean total weight loss per kg of subject, per period, was obtained by calculating the difference between the highest and lowest subject's total weight loss per period.

The determination of the subjects' weight, subjects' ideal weight, nitrogen balance, nitrogen intake, nitrogen losses, mean protein loss, mean tissue loss, mean nitrogen loss per kilo per period and the range of mean nitrogen loss per kilo period was carried out according to the methodology of Example 1.

RESULTS OF THE STUDY
GROUP "1" NITROGEN BALANCE RESULTS BY DIET

| Diet | D | E | F |
|---|---|---|---|
| Group 1 | negative | negative | equilibrium |

The following are the results obtained from the Group "1" comprised of twenty-four subjects, during each 28 day diet period:

| Period: 28 days | Subjects: 24 |
|---|---|
| DURING DIET "D" | |
| NITROGEN BALANCE per subject per period: | NEGATIVE* |
| Mean Nitrogen Loss per subject per period: | 75.830 g |
| Mean Nitrogen Loss per kg per period: | 940 mg |
| Mean Protein Loss per subject per period: | 473.94 g |
| Mean Lean Tissue Loss per subject per period: | 2,370 g |
| Mean Initial Weight per subject: | 84,100 g |
| Mean Final Weight per subject: | 77,200 g |
| Mean Total Weight Loss per subject: | 6,900 g |
| Mean Fat Loss per subject: | 4,530 g |
| DURING DIET "E" | |
| NITROGEN BALANCE per subject per period: | NEGATIVE* |
| Mean Nitrogen Loss per subject per period: | 33.116 g |
| Mean Nitrogen Loss per kg per period: | 447 mg |
| Mean Protein Loss per subject per period: | 206.975 g |
| Mean Lean Tissue Loss per subject per period: | 1,035 g |
| Mean Initial Weight per subject: | 77,200 g |
| Mean Final Weight per subject: | 70,700 g |
| Mean Total Weight Loss per subject: | 6,500 g |
| Mean Fat Loss per subject: | 5,465 g |
| DURING DIET "F" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |
| Mean Initial Weight per subject: | 70,700 g |
| Mean Final Weight per subject: | 64,000 g |
| Mean Total Weight Loss per subject: | 6,700 g |
| Mean Fat Loss per subject: | 6,700 g |

*found in all twenty-four subjects.

GROUP "2" NITROGEN BALANCE RESULTS BY DIET

| Diet | E | F | D |
|---|---|---|---|
| Group 2 | negative | equilibrium | negative |

The following are the results obtained from the Group "2" comprised of twenty-four subjects, during each 28 day diet period:

| Period: 28 days | Subjects: 24 |
|---|---|
| DURING DIET "E" | |
| NITROGEN BALANCE per subject per period: | NEGATIVE* |
| Mean Nitrogen Loss per subject per period: | 37.773 g |
| Mean Nitrogen Loss per kg per period: | 384 mg |
| Mean Protein Loss per subject per period: | 236.081 g |
| Mean Lean Tissue Loss per subject per period: | 1.180 g |
| Mean Initial Weight per subject: | 102,200 g |
| Mean Final Weight per subject: | 94,100 g |
| Mean Total Weight Loss per subject: | 8,100 g |
| Mean Fat Loss per subject: | 6,920 g |
| DURING DIET "F" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |
| Mean Initial Weight per subject: | 94,100 g |
| Mean Final Weight per subject: | 85,600 g |
| Mean Total Loss per subject: | 8,500 g |
| Mean Fat Loss per subject: | 8,500 g |
| DURING DIET "D" | |
| NITROGEN BALANCE per subject per subject: | NEGATIVE* |
| Mean Nitrogen Loss per subject per period: | 81.710 g |
| Mean Nitrogen Loss per kg per period: | 996 mg |
| Mean Protein Loss per subject per period: | 510.690 g |
| Mean Lean Tissue Loss per subject per period: | 2,553 g |
| Mean Initial Weight per subject: | 85,600 g |
| Mean Final Weight per subject: | 78,400 g |
| Mean Total Weight Loss per subject: | 7,200 g |
| Mean Fat Loss per subject: | 4,647 g |

*found in all twenty-four subjects.

GROUP "3" NITROGEN BALANCE RESULTS BY DIET

| Diet | F | D | E |
|---|---|---|---|
| Group 3 | equilibrium | negative | negative |

The following are the results obtained from the Group "3" comprised of twenty-four subjects, during each 28 day diet period:

| Period: 28 days | Subjects: 24 |
|---|---|
| DURING DIET "F" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |
| Mean Initial Weight per subject: | 76,300 g |
| Mean Final Weight per subject: | 68,800 g |
| Mean Total Weight Loss per subject: | 7,500 g |
| Mean Fat Loss per subject: | 7,500 g |
| DURING DIET "D" | |
| NITROGEN BALANCE per subject per period: | NEGATIVE* |
| Mean Nitrogen Loss per subject per period: | 59.528 g |
| Mean Nitrogen Loss per kg per period: | 910 mg |
| Mean Protein Loss per subject per period: | 372.050 g |
| Mean Lean Tissue Loss per subject per period: | 1.860 g |
| Mean Initial Weight per subject: | 68,800 g |
| Mean Final Weight per subject: | 61,900 g |
| Mean Total Weight Loss per subject: | 6,900 g |
| Mean Fat Loss per subject: | 5,040 g |
| DURING DIET "E" | |
| NITROGEN BALANCE per subject per period: | NEGATIVE* |
| Mean Nitrogen Loss per subject per period: | 26.713 g |
| Mean Nitrogen Loss per kg per period: | 455 mg |
| Mean Protein Loss per subject per period: | 207.006 g |
| Mean Lean Tissue Loss per subject per period: | 1,035 g |
| Mean Initial Weight per subject: | 61,900 g |
| Mean Final Weight per subject: | 55,400 g |
| Mean Total Weight Loss per subject: | 6,500 g |
| Mean Fat Loss per subject: | 5,465 g |

*found in all twenty-four subjects.

| NITROGEN BALANCE RESULTS BY GROUP AND DIET | | | |
|---|---|---|---|
| Diet | D | E | F |
| Group 1 | equilibrium | negative | negative |
| Group 2 | equilibrium | negative | negative |
| Group 3 | equilibrium | negative | negative |

The following are the results obtained from the Groups 1, 2, and 3, comprised of seventy-two subjects, during each 28 day diet period:

| Period: 28 days | Subjects: 72 |
|---|---|
| DURING DIET "D" | |
| NITROGEN BALANCE per subject per period: | NEGATIVE* |
| Mean Nitrogen Loss per subject per period: | 72.356 g |
| Mean Nitrogen Loss per kg per period: | 952 mg |
| Range of Mean Nitrogen Loss per kg per period: | 45 mg |
| Mean Protein Loss per subject per period: | 452.225 g |
| Mean Lean Tissue Loss per subject per period: | 2,261 g |
| Mean Initial Weight per subject: | 79,500 g |
| Mean Final Weight per subject: | 72,500 g |
| Mean Total Weight Loss per subject: | 7,000 g |
| Mean Total Weight Loss per kg per period: | 92 g |
| Range of Mean Total Weight Loss per kg per period: | 9 g |
| Mean Fat Loss per subject: | 4,739 g |
| DURING DIET "E" | |
| NITROGEN BALANCE per subject per period: | NEGATIVE* |
| Mean Nitrogen Loss per subject per period: | 31.200 g |
| Mean Nitrogen Loss per kg per period: | 405 mg |
| Range of Mean Nitrogen Loss per kg per period: | 21 mg |
| Mean Protein Loss per subject per period: | 195.000 mg |
| Mean Lean Tissue Loss per subject per period: | 975 g |
| Mean Initial Weight per subject: | 80,433 g |
| Mean Final Weight per subject: | 73,400 g |
| Mean Total Weight Loss per subject: | 7,033 g |
| Mean Total Weight Loss per kg per period: | 91 g |
| Range of Mean Total Weight Loss per kg per period: | 7 g |
| Mean Fat Loss per subject: | 6,058 g |
| DURING DIET "F" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |
| Mean Initial Weight per subject: | 80,366 g |
| Mean Final Weight per subject: | 72,800 g |
| Mean Total Weight Loss per subject: | 7,566 g |
| Mean Total Weight Loss per kg per period: | 98 g |
| Range of Mean Total Weight Loss per kg per period: | 6 g |
| Mean Fat Loss per subject: | 7,566 g |

*found in all seventy-two subjects.

The data in Table VII shows the mean percentage of weight loss per patient per diet per period.

TABLE VII

| | Lean Tissue Loss | Fat Loss | Total Loss |
|---|---|---|---|
| Diet "D" | 32% | 68% | 100% |
| Diet "E" | 14% | 86% | 100% |
| Diet "F" | 0% | 100% | 100% |

Considering that the seventy-two subjects of this study had:

(a) the same protein intake from Diets E and F, which was 0.4 g/Kg/day, equivalent to 64 mg/Kg/day of nitrogen;

(b) the same energy intake from Diets D, E and F, which was equivalent to 12 Kcal/Kg/day; and (c) the same daily vitamins and minerals supplement, which was in accordance with the US Recommended Daily Allowance.

The seventy-two subjects have shown:

(a) the highest net nitrogen utilization (NNU) (Table VII) when receiving formula of Table I, during the periods of Diet F, by achieving an "equilibrium" in their nitrogen balances, which was not achieved during the periods of Diet E (casein formula) and Diet D (water diets).

TABLE VIII

SUBJECTS MEAN APPARENT NET NITROGEN UTILIZATION DURING THE STUDY × 100

| Protein Source | Nitrogen intake | Nitrogen output | NNU result | +/− |
|---|---|---|---|---|
| Diet D | 0 | 100 | 0% | −100% |
| Diet E | 100 | 143 | 57% | −43% |
| Diet F | 100 | 100 | 100%* | 0% |

*This is a hypothetical 100% based on the fact that nitrogen intake and output are essentially in balance.

(b) a lower net nitrogen utilization (NNU) (Table VIII) when receiving casein amino acid formula during the periods of diet by obtaining negative nitrogen balances, with a mean nitrogen loss per subject equivalent to 405 mg/Kg/period, which was 43% less NNU than when receiving the formula of Table I during Diet F periods;

(c) the lowest net nitrogen utilization (NNU) (Table VIII) when receiving Diet D (water diet) by obtaining negative nitrogen balances, with a mean nitrogen loss per subject equivalent to 952 mg/kg/period, which was 100% less NNU than when receiving the formula of Table I during Diet F periods;

(d) a fat loss of 100% of the mean total weight loss, when receiving the formula of Table I during Diet F periods (Table VII);

(e) a mean of 86% fat and 14% lean tissue losses, of the mean total weight loss, when receiving casein amino acid formula during Diet E periods (Table VII); and (f) a mean of 68% fat and 32% lean tissue losses, of the mean total weight loss, when receiving the water diet during Diet D periods (Table VII).

For these reasons, it is apparent that the seventy-two subjects, receiving the formula of Table I during Diet F periods, have provided evidence that:

(a) the highest net nitrogen utilization (NNU), which was 43% more than when receiving casein amino acid formula during Diet E periods, and 100% more than when receiving water diet during Diet D periods (Table VIII);

(b) the total preservation of lean tissue, which was 14% more than when receiving casein amino acid formula and 32% more than when receiving the water diet (Table VII); and (c) the highest fat loss, which was 20% more than when receiving casein amino acid formula and 37% more than when receiving water diet (Table VII).

The formula of Table I has shown superior characteristics as a weight-loss diet, when compared to a casein amino acid formula or to water diets, because it results in higher fat loss, a higher net nitrogen utilization (NNU), and the total preservation of the subject's lean tissue. These results show that the composition of the invention provides surprising and unexpected results for the treatment and prevention of obesity.

EXAMPLE 3

This example compares the results obtained with the applicants composition with the results obtained from feeding dried bovine milk, supplemented dried bovine milk, soybean flour and supplemented soybean flour.

This study was a comparative double-blind, quintuple cross-over study that was carried out in thirty subjects, during a 100 day period, to examine subjects' nitrogen balances, in order to determine the net nitrogen utilization (NNU) of consumed protein or protein with the addition of an amino acid supplement, during Diets G, H, I, J and K. The preliminary phase was carried out over a thirty day period in accordance with the procedure of Example 1.

At the beginning of the main phase, thirty healthy subjects were randomly chosen to be integrated into five matched groups, according to sex and number, and named Groups 1, 2, 3, 4 and 5. The main phase, conducted during five consecutive 14 day periods, had the purpose of examining, during Diets G, H, I, J, and K, the subjects' nitrogen balances, in order to determine the subjects' net nitrogen utilization (NNU). To achieve this purpose, Groups 1, 2, 3, 4 and 5 each comprised of six healthy subjects, were fed with Diets G, H, I, J and K, according to the sequence of Table IX.

TABLE IX

| SEQUENCE OF THE DIETS BY GROUPS | | | | | | |
|---|---|---|---|---|---|---|
| GROUP 1 | MESD | G | H | I | J | K |
| GROUP 2 | MESD | H | I | J | K | G |
| GROUP 3 | MESD | I | J | K | G | H |
| GROUP 4 | MESD | J | K | G | H | I |

TABLE IX-continued

| SEQUENCE OF THE DIETS BY GROUPS | | | | | | |
|---|---|---|---|---|---|---|
| GROUP 5 | MESD | K | G | H | I | J |

The study population comprised thirty healthy subjects, fifteen males and fifteen females, aged from 22 to 38 years (mean age 27).

The thirty healthy subjects were randomly chosen and matched to be integrated, according to sex and number, into five equal Groups, named groups 1, 2, 3, 4 and 5.

GROUP "1" comprised six healthy subjects, three males and three females, aged from 24 to 36 years (mean age 26), who were randomly chosen.

GROUP "2" comprised six healthy subjects, three males and three females, aged from 24 to 35 years (mean age 29), who were randomly chosen.

GROUP "3" comprised six healthy subjects, three males and three females, aged from 22 to 38 years (mean age 27), who were randomly chosen.

GROUP "4" comprised six healthy subjects, three males and three females, aged from 23 to 36 years (mean age 26), who were randomly chosen.

GROUP "5" comprised six healthy subjects, three males and three females, aged from 22 to 34 years (mean age 26), who were randomly chosen.

The following criteria was used for subject selection:
(a) the subject had to be in good health;
(b) the subject could not be under-weight; and
(c) the subject could not be pregnant.

The following criteria was used to exclude a subject during the study:
(a) the subject who became sick, thus altering his/her nitrogen balance;
(b) the subject who expressed his/her desire not to continue in this study;
(c) the subject who did not follow the prescribed rules of the study; and
(d) the subject who became pregnant.

After the MESD conclusion, at the beginning of the main phase, the thirty healthy subjects were randomly chosen and matched to be integrated, according to sex and number, into five equal groups, named Groups 1, 2, 3, 4 and 5.

In accordance with the diet sequence (Table IX), the main phase of this study, was conducted during five consecutive 14 day periods, with the purpose of examining the subjects' nitrogen balances during the periods of Diets "G" (dried bovine milk), "H" (supplemented dried bovine milk, "I" (soybean flour), "J" (supplemented soybean flour), and "K" (formula of Table I), in order to evaluate the subjects' NNU. To achieve this purpose, Groups 1, 2, 3, 4 and 5 each one comprised of six healthy subjects, were fed with Diets G, H, I, J and K following a sequence of Table IX.

Diets G, H, I, J and K consisted of an identical composition of protein, carbohydrate, fat, vitamins and minerals, but of a different protein source, had the following characteristics:

DIET "G" provided to the subject, a protein intake of 0.4 g/Kg/day, equivalent to 64 mg/Kg/day of nitrogen, from dried bovine milk (Table X) and an energy intake of 50 Kcal/Kg/day, from protein-free carbohydrate and fat (Table IA).

DIET "H" provided to the subject a protein intake of 0.4 g/Kg/day, equivalent to 64 mg/Kg/day of nitrogen, from dried bovine milk, with the addition of an amino acids supplement, as set forth in Table X, to duplicate the formula of Table I as close as possible and an energy intake of 50 Kcal/Kg/day, from protein-free carbohydrate and fat (Table IA).

DIET "I" provided to the subject, a protein intake of 0.4 g/Kg/day, equivalent to 64 mg/Kg/day of nitrogen, from soybean flour and an energy intake of 50 Kcal/Kg/day, from protein-free carbohydrate and fat (Table IA).

DIET "J" provided to the subject a protein intake of 0.4 g/Kg/day, equivalent to 64 mg/Kg/day of nitrogen, from soybean with the addition of an amino acids supplement from Table XI to duplicate the formula of Table I as close as possible and an energy intake of 50 Kcal/Kg/day, from protein-free carbohydrate and fat (Table IA).

DIET "K" provided to the subject a protein intake of 0.4 g/Kg/day, equivalent to 64 mg/Kg/day of nitrogen, from the formula of Table I, and an energy intake of 50 Kcal/Kg/day, from protein-free carbohydrate and fat (Table IA).

To avoid common errors in determining nitrogen intake, which could affect the nitrogen balance, the carbohydrate and fat of Diets G, H, and I, were protein-free.

To avoid common errors in determining energy intake, which could also affect nitrogen balance, Diets G, H, I, J, and K supplied a constant energy intake per subject equivalent to 50 Kcal/Kg/day, during each 14 day period.

To avoid over-estimating nitrogen intake, caused by unconsumed daily protein or amino acids formulas, during each 14 day period, all thirty subjects were fed three times per day at 8:00 a.m.; 2:00 p.m., and 8:00 p.m., achieving the total consumption of their allotted formula.

To avoid errors in determining energy intake, which could affect nitrogen balance, formulas given during Diets G, H, I, J and K has an equivalent composition of protein, with the same energy intake.

To avoid the identification by the subject of his/her formula by its flavor, which could affect the double-blind characteristic of this study, the formulas of Diets G, H, I, J and K were mixed with a common fruit shake. To avoid errors in energy intake, this fruit shake, by itself, provided the same enery intake. The fruit for the shake, was changed almost daily, and was chosen from the fruits of Example I.

To avoid a nitrogen over-intake per g/Kg/day, which could affect the nitrogen balance, the subjects' protein requirement was calculated in accordance with his/her ideal weight.

A daily vitamin and minerals supplement according to Example 4 was given to all thirty subjects, during the 70 day period.

Determining Mean Nitrogen Loss

The subjects' mean nitrogen loss per kg per period, was obtained by dividing the subjects' mean nitrogen loss per period by the mean ideal weight.

The methods for determining the subjects' weight, subjects' ideal weight, nitrogen balance, nitrogen intake, nitrogen losses, mean protein loss, mean tissue loss, lean tissue, mean nitrogen loss per kilo per pound, and range of mean nitrogen losses are set forth in Example 1.

The following were the results of the nitrogen balance results by diet:

| | GROUP I | | | | |
|---|---|---|---|---|---|
| Diet | G | H | I | J | K |
| Group I | Neg # | Neg | Neg | Neg | Equi* |
| # Negative | | | | | *Equilibrium |

The following are the results obtained from the Group "1" comprised of six subjects, with a mean ideal weight of 54 kg, during each 14 day diet period:

| Period: 14 days | Subjects: 6 |
|---|---|
| DURING DIET "G" | |
| NITROGEN BALANCE per subject per period: | NEGATIVE* |
| Mean Nitrogen Loss per subject per period: | 26.611 g |
| Mean Nitrogen Loss per kg per period: | 493 mg |
| Mean Protein Loss per subject per period: | 166 g |
| Mean Lean Tissue Loss per subject per period: | 831 g |
| DURING DIET "H" | |
| NITROGEN BALANCE per subject per period: | NEGATIVE* |
| Mean Nitrogen Loss per subject per period: | 10.629 g |
| Mean Nitrogen Loss per kg per period: | 197 mg |
| Mean Protein Loss per subject per period: | 66 g |
| Mean Lean Tissue Loss per subject per period: | 332 g |
| DURING DIET "I" | |
| NITROGEN BALANCE per subject per period: | NEGATIVE* |
| Mean Nitrogen Loss per subject per period: | 32.888 g |
| Mean Nitrogen Loss per kg per period: | 609 mg |
| Mean Protein Loss per subject per period: | 205 g |
| Mean Lean Tissue Loss per subject per period: | 1.027 g |
| DURING DIET "J" | |
| NITROGEN BALANCE per subject per period: | NEGATIVE* |
| Mean Nitrogen Loss per subject per period: | 12.529 g |
| Mean Nitrogen Loss per kg per period: | 232 mg |
| Mean Protein Loss per subject per period: | 78 g |
| Mean Lean Tissue Loss per subject per period: | 391 g |
| DURING DIET "K" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |

*found in all six subjects.

| GROUP "2" NITROGEN BALANCE RESULTS BY DIET | | | | | |
|---|---|---|---|---|---|
| Diet | H | I | J | K | G |
| Group 2 | Neg # | Neg | Neg | Equi* | Neg |
| # Negative | | | | *Equilibrium | |

The following are the results obtained from the Group "2" comprised of six subjects, with a mean ideal weight of 53.5 kg, during each 14 day diet period:

| Period: 14 days | Subjects: 6 |
|---|---|
| DURING DIET "H" | |
| NITROGEN BALANCE per subject per period: | NEGATIVE* |
| Mean Nitrogen Loss per subject per period: | 10.541 g |
| Mean Nitrogen Loss per kg per period: | 197 mg |
| Mean Protein Loss per subject per period: | 65 g |
| Mean Lean Tissue Loss per subject per period: | 329 g |
| DURING DIET "I" | |
| NITROGEN BALANCE per subject per period: | NEGATIVE* |
| Mean Nitrogen Loss per subject per period: | 32.527 g |

| Period: 14 days | Subjects: 6 |
|---|---|
| Mean Nitrogen Loss per kg per period: | 608 mg |
| Mean Protein Loss per subject per period: | 203 g |
| Mean Lean Tissue Loss per subject per period: | 1,016 g |
| DURING DIET "J" | |
| NITROGEN BALANCE per subject per period: | NEGATIVE* |
| Mean Nitrogen Loss per subject per period: | 12.303 g |
| Mean Nitrogen Loss per kg per period: | 230 mg |
| Mean Protein Loss per subject per period: | 76 g |
| Mean Lean Tissue Loss per subject per period: | 384 g |
| DURING DIET "K" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |
| DURING DIET "G" | |
| NITROGEN BALANCE per subject per period: | NEGATIVE* |
| Mean Nitrogen Loss per subject per period: | 26.428 g |
| Mean Nitrogen Loss per kg per period: | 494 mg |
| Mean Protein Loss per subject per period: | 165 g |
| Mean Lean Tissue Loss per subject per period: | 825 g |

*found in all six subjects.

| GROUP "3" NITROGEN BALANCE RESULTS BY DIET | | | | | |
|---|---|---|---|---|---|
| Diet | I | J | K | G | H |
| Group 3 | Neg # | Neg | Equi* | Neg | Neg |

Negative
*Equilibrium

The following are the results obtained from the Group "3" comprised of six subjects, with a mean weight of 54.5 kg, during each 14 day diet period:

| Period: 14 days | Subjects: 6 |
|---|---|
| DURING DIET "I" | |
| NITROGEN BALANCE per subject per period: | NEGATIVE* |
| Mean Nitrogen Loss per subject per period: | 33.191 g |
| Mean Nitrogen Loss per kg per period: | 609 mg |
| Mean Protein Loss per subject per period: | 207 g |
| Mean Lean Tissue Loss per subject per period: | 1,037 g |
| DURING DIET "J" | |
| NITROGEN BALANCE per subject per period: | NEGATIVE* |
| Mean Nitrogen Loss per subject per period: | 12.588 g |
| Mean Nitrogen Loss per kg per period: | 231 mg |
| Mean Protein Loss per subject per period: | 78 g |
| Mean Lean Tissue Loss per subject per period: | 393 g |
| DURING DIET "K" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |
| DURING DIET "G" | |
| NITROGEN BALANCE per subject per period: | NEGATIVE* |
| Mean Nitrogen Loss per subject per period: | 26.866 g |
| Men Nitrogen Loss per kg per period: | 493 mg |
| Mean Protein Loss per subject per period: | 167 g |
| Mean Lean Tissue Loss per subject per period: | 839 g |
| DURING DIET "H" | |
| NITROGEN BALANCE per subject per period: | NEGATIVE* |
| Mean Nitrogen Loss per subject per period: | 10.629 g |
| Mean Nitrogen Loss per kg per period: | 195 mg |
| Mean Protein Loss per subject per period: | 66 g |
| Mean Lean Tissue Loss per subject per period: | 332 g |

*found in all six subjects.

| GROUP "4" NITROGEN BALANCE RESULTS BY DIET | | | | | |
|---|---|---|---|---|---|
| Diet | J | K | G | H | I |
| Group 4 | Neg# | Equi* | Neg | Neg | Neg |

Negative
*Equilibrium

The following are the results obtained from the Group "4" comprised of six subjects, with a mean ideal weight of 53.5 kg, during each 14 day diet period:

| Period: 14 days | Subjects: 6 |
|---|---|
| DURING DIET "J" | |
| NITROGEN BALANCE per subject per period: | NEGATIVE* |
| Mean Nitrogen Loss per subject per period: | 12.466 g |
| Mean Nitrogen Loss per kg per period: | 233 mg |
| Mean Protein Loss per subject per period: | 77 g |
| Mean Lean Tissue Loss per subject per period: | 389 g |
| DURING DIET "K" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |
| DURING DIET "G" | |
| NITROGEN BALANCE per subject per period: | NEGATIVE* |
| Mean Nitrogen Loss per subject per period: | 26.480 g |
| Mean Nitrogen Loss per kg per period: | 495 mg |
| Mean Protein Loss per subject per period: | 165 g |
| Mean Lean Tissue Loss per subject per period: | 827 g |
| DURING DIET "H" | |
| NITROGEN BALANCE per subject per period: | NEGATIVE* |
| Mean Nitrogen Loss per subject per period: | 10.490 g |
| Mean Nitrogen Loss per kg per period: | 196 mg |
| Mean Protein Loss per subject per period: | 65 g |
| Mean Lean Tissue Loss per subject per period: | 327 g |
| DURING DIET "I" | |
| NITROGEN BALANCE per subject per period: | NEGATIVE* |
| Mean Nitrogen Loss per subject per period: | 32.633 g |
| Mean Nitrogen Loss per kg per period: | 610 mg |
| Mean Protein Loss per subject per period: | 203 g |
| Mean Lean Tissue Loss per subject per period: | 1,019 g |

*found in all six subjects.

| GROUP "5" NITROGEN BALANCE RESULTS BY DIET | | | | | |
|---|---|---|---|---|---|
| Diet | K | G | H | I | J |
| Group 5 | Equi* | Neg# | Neg | Neg | Neg |

*Equilibrium
Negative

The following are the results obtained from the Group "5" comprised of six subjects, with a mean ideal weight of 55 kg, during each 14 day diet period:

| Period: 14 days | Subjects: 6 |
|---|---|
| DURING DIET "K" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |
| DURING DIET "G" | |
| NITROGEN BALANCE per subject per period: | NEGATIVE* |
| Mean Nitrogen Loss per subject per period: | 27.174 g |
| Mean Nitrogen Loss per kg per period: | 494 mg |
| Mean Protein Loss per subject per period: | 169 g |

| Period: 14 days | Subjects: 6 |
|---|---|
| Mean Lean Tissue Loss per subject per period: | 849 g |
| DURING DIET "H" | |
| NITROGEN BALANCE per subject per period: | NEGATIVE* |
| Mean Nitrogen Loss per subject per period: | 10.830 g |
| Mean Nitrogen Loss per kg per period: | 197 mg |
| Mean Protein Loss per subject per period: | 67 g |
| Mean Lean Tissue Loss per subject per period: | 338 g |
| DURING DIET "I" | |
| NITROGEN BALANCE per subject per period: | NEGATIVE* |
| Mean Nitrogen Loss per subject per period: | 33.449 g |
| Mean Nitrogen Loss per kg per period: | 608 mg |
| Mean Protein Loss per subject per period: | 209 g |
| Mean Lean Tissue Loss per subject per period: | 1.045 g |
| DURING DIET "J" | |
| NITROGEN BALANCE per subject per period: | NEGATIVE* |
| Mean Nitrogen Loss per subject per period: | 12.818 g |
| Mean Nitrogen Loss per kg per period: | 233 mg |
| Mean Protein Loss per subject per period: | 81 g |
| Mean Lean Tissue Loss per subject per period: | 400 g |

*found in all six subjects.

| NITROGEN BALANCE RESULTS BY GROUP AND DIET | | | | | |
|---|---|---|---|---|---|
| Diet | G | H | I | J | K |
| Group 1 | Neg# | Neg | Neg | Neg | Equi* |
| Group 2 | Neg | Neg | Neg | Neg | Equi |
| Group 3 | Neg | Neg | Neg | Neg | Equi |
| Group 4 | Neg | Neg | Neg | Neg | Equi |
| Group 5 | Neg | Neg | Neg | Neg | Equi |

Negative
*Equilibrium

The following are the results obtained from the Groups 1, 2, 3, 4 and 5 comprised of thirty subjects, with a mean ideal weight of 54 kg, during each 14 day diet period:

| Period: 14 days | Subjects: 30 |
|---|---|
| DURING DIET "G" | |
| NITROGEN BALANCE per subject per period: | NEGATIVE* |
| Mean Nitrogen Loss per subject per period: | 26.712 g |
| Mean Nitrogen Loss per kg per period: | 495 mg |
| Range of Mean Nitrogen Loss per kg per period: | 22 mg |
| Mean Protein Loss per subject per period: | 166 g |
| Mean Lean Tissue Loss per subject per period: | 834 g |
| DURING DIET "H" | |
| NITROGEN BALANCE per subject per period: | NEGATIVE* |
| Mean Nitrogen Loss per subject per period: | 10.623 g |
| Mean Nitrogen Loss per kg per period: | 197 mg |
| Range of Mean Nitrogen Loss per kg per period: | 8 mg |
| Mean Protein Loss per subject per period: | 66 g |
| Mean Lean Tissue Loss per subject per period: | 331 g |
| DURING DIET "I" | |
| NITROGEN BALANCE per subject per period: | NEGATIVE* |
| Mean Nitrogen Loss per subject per period: | 32.937 g |
| Mean Nitrogen Loss per kg per period: | 610 mg |
| Range of Mean Nitrogen Loss per kg per period: | 27 mg |
| Mean Protein Loss per subject per period: | 205 g |
| Mean Lean Tissue Loss per subject per period: | 1,029 g |
| DURING DIET "J" | |
| NITROGEN BALANCE per subject per period: | NEGATIVE* |
| Mean Nitrogen Loss per subject per period: | 12.540 g |
| Mean Nitrogen Loss per kg per period: | 232 mg |
| Range of Mean Nitrogen Loss per kg per period: | 11 mg |
| Mean Protein Loss per subject per period: | 78 g |
| Mean Lean Tissue Loss per subject per period: | 391 g |

| Period: 14 days | Subjects: 30 |
|---|---|
| DURING DIET "K" | |
| NITROGEN BALANCE per subject per period: | EQUILIBRIUM* |
| Mean Nitrogen Loss per subject per period: | NONE |
| Mean Protein Loss per subject per period: | NONE |
| Mean Lean Tissue Loss per subject per period: | NONE |

*found in all thirty subjects.

The thirty subjects have shown:

(a) the highest net nitrogen utilization (NNU) when receiving the formula of Table I during the periods of Diet K, by achieving an "equilibrium" in their nitrogen balances, which was not achieved during the periods of Diet G (dried bovine milk), Diet H (supplemented dried bovine milk), Diet I (soybean flour) or Diet J (supplemented soybean flour);

(b) a lower net nitrogen utilization (NNU) when receiving supplemented dried bovine milk during the periods of Diet H, by obtaining negative nitrogen balances, with a mean nitrogen loss per subject equivalent to 197 mg/kg/period, which was 22% less NNU than when receiving the formula of Table I during the Diet K periods;

(c) a lower net nitrogen utilization (NNU) when receiving dried bovine milk during the periods of Diet G, by obtaining negative nitrogen balances, with a mean nitrogen loss per subject equivalent to 495 mg/kg/period, which was 55% less NNU than when receiving the formula of Table I during Diet K periods;

(d) a lower net nitrogen utilization (NNU) when receiving supplemented soybean flour, during the periods of Diet J, by obtaining negative nitrogen balances, with a mean nitrogen loss per subject equivalent to 232 mg/kg/period, which was 26% less NNU than when receiving the formula of Table I during Diet K periods; and (e) the lowest net nitrogen utilization (NNU) when receiving soybean flour during the periods of Diet I, by obtaining negative nitrogen balances, with a mean nitrogen loss per subject equivalent to 610 mg/kg/period, which was 68% less NNU than when receiving the formula of Table I during the Diet K periods.

Considering that it has been overwhelmingly demonstrated, throughout this double-blind quintuple crossover study, that the thirty subjects have shown:

(a) no lean tissue loss, when receiving the formula of Table I during Diet K periods;

(b) a mean of 834 g per period of subject's lean tissue loss, when receiving dried bovine milk, during Diet G periods;

(c) a mean of 331 g per period of subject's lean tissue loss, when receiving supplemented dried bovine milk, during Diet H periods;

(d) a mean of 1.029 g per period of subject's lean tissue loss, when receiving soybean flour during Diet I periods; and (e) a mean of 391 g per period of subject's lean tissue loss, when receiving supplemented soybean flour, during Diet J periods.

The thirty subjects, had the highest net nitrogen utilization (NNU) when receiving the formula of Table I during the periods of Diet K, by achieving an "equilibrium" in their nitrogen balances, which was:

(a) a 68% more NNU than when receiving soybean flour during Diet I periods;

(b) a 55% more NNU than when receiving dried bovine milk during Diet G periods;

(c) a 26% more NNU than when receiving supplemented soybean flour during Diet J periods; and (d) a 22% more NNU than when receiving supplemented dried bovine milk, during Diet H periods.

When receiving amino acids supplemented dried bovine or soybean flour diets, in order to duplicate as close as possible the formula of Table I, our thirty subjects have shown:

(a) a 33% more NNU receiving supplemented dried bovine milk during Diet H periods, than when receiving non supplemented dried bovine milk during Diet G periods; and (b) a 42% more NNU receiving supplemented soybean flour during Diet J periods, than when receiving non-supplemented soybean flour, during Diet I periods.

The formula of Table I has shown superior results as these foods compared to dried bovine milk or soybean flour, even when supplemented, by achieving the subject's highest NNU, and consequentially, total preservation of the subjects' lean tissue.

TABLE X

| | Essential Amino Acid Composition of Dried Bovine Milk* (g/10 g of essential amino acid content) | Added Amino Acid Complement (g added/10 g of essential amino acid content) |
|---|---|---|
| isoleucine | 1.443 | 0 |
| leucine | 2.226 | 0.061 |
| lysine | 1.760 | 0 |
| methionine | 0.556 | 0 |
| phenylalanine | 1.100 | 0 |
| threonine | 1.041 | 0.185 |
| tryptophan | 0.317 | 0.131 |
| valine | 1.553 | 0.168 |

*Based on the data presented in Orr, M. L., and Watt, B. K., "Amino Acid Content of Foods", U.S. Dept. Agr., 1957.

TABLE XI

| | Essential Amino Acid Composition of Soybean* Flour (g/10 g of essential amino acid content) | Added Amino Acid Complement (g added/10 g of essential amino acid content) |
|---|---|---|
| isoleucine | 1.548 | 0 |
| leucine | 2.220 | 0.067 |
| lysine | 1.819 | 0 |
| methionine | 0.386 | 0 |
| phenylalanine | 1.423 | 0 |
| threonine | 0.691 | 0.535 |
| tryptophan | 0.396 | 0.052 |
| valine | 1.511 | 0.210 |

*Based on the data presented in Orr, M. L., and Watt, B. K., "Amino Acid Content of Foods", U.S. Dept. Agr., 1957.

EXAMPLE 4

An example of a vitamin-mineral composition which may be administered for each gram of amino acid administered.

| | wt. | % |
|---|---|---|
| Sodium (as NaCl) | 18.00 mg | 10.5 |
| Potassium (KCl) | 55.00 mg | 32.35 |
| Magnesium (MgO) | 3.80 mg | 2.23 |
| Calcium (CaCo$_3$) | 31.00 mg | 18.23 |
| Manganese (MmSO$_4$) | 1.40 mcg | 0.00082 |
| Iron (Fe fumarate) | 50.00 mcg | 0.029 |

-continued

| | wt. | % |
|---|---|---|
| Cobalt (Co) | 1.40 mcg | 0.00082 |
| Copper (CuO) | 50.00 mcg | 0.029 |
| Zinc (ZnO) | 0.22 mg | 0.129 |
| Nickel (NiO) | 1.00 mcg | 0.00058 |
| Chromium (CrCl$_3$) | 6.7 mg | 0.039 |
| Molybdenum (Na molybdate) | 1.00 mcg | 0.00058 |
| Vanadium (Vachelate) | 0.50 mcg | 0.00029 |
| Phosphorus ( ) | 15.00 mg | 8.824 |
| Chloride (Kcl, N$_a$Cl) | 40.00 mg | 23.53 |
| Fluoride (N$_a$F) | 17.00 mcg | 0.010 |
| Iodine (KI) | 6.30 mcg | 0.0037 |
| Selenium (org chelate) | 3.30 mcg | 0.0019 |
| Bromine (K Bi) | 0.10 mcg | 0.058 |
| Boron (H$_3$BO$_3$) | 60.0 mcg | 0.0035 |
| Silicon (kelp) | 0.30 mg | 0.017 |
| Vitamin A (acetate) | 86.00 mcg | 0.049 |
| Vitamin D (ergosterol) | 50.00 ng | 0.00029 |
| Alpha-tocopherol | 0.104 mcg | 0.610 |
| Vitamin K | 3.00 mcg | 0.0017 |
| Vitamin B1 | 15.00 mcg | 0.0088 |
| Vitamin B2 (riboflavin) | 38.00 mcg | 0.022 |
| Nicotinamide | 0.18 mg | 0.105 |
| Pantothenic Acid (capanthothenate) | 0.24 mg | 0.141 |
| Vitamin 6 | 18.00 mcg | 0.010 |
| Biotin | 0.58 mcg | 0.00034 |
| Folic Acid | 5.00 mcg | 0.0029 |
| Vitamin B12 (cyanocobalamin) | 50.00 ng | 0.00029 |
| Vitamin C (ascorbic acid) | 5.00 mg | 2.94 |

The particular source of the mineral or vitamin is not critical and any suitable source can be used. Remington Practice of Pharmacy, 17 Ed. pp. 1004-1034, describes the various sources of vitamins and minerals and these pages are incorporated by reference.

I claim:

1. A nutritional composition comprising which consists essentially of a combination of the following:

(a) isoleucine, leucine, lysine, methionine, phenylalanine, threonine, tryptophan, and valine in amounts relative to one another which will provide a Net Nitrogen Utilization (NNU) of at least 80%;

(b) a carbohydrate selected from the group consisting of sucrose, maltose and sorbitol, and a highly polyunsaturated vegetable fat selected from the group consisting of safflower oil, sunflower oil and corn oil; and (c) for each gram of amino acid, an amount of vitamins which is equivalent to the following:

| Vitamin A | 60.0–109.0 mcg |
|---|---|
| Vitamin D | 37.0–63.0 ng |
| Alpha-tocopherol | 0.078–0.130 mg |
| Vitamin K | 2.0–4.0 mcg |
| Vitamin B$_1$ | 10.0–20.0 mcg |
| Vitamin B$_2$ | 27.0–48.0 mcg |
| Nicotinamide | 0.13–0.23 mg |
| Pantothenic Acid | 0.18–0.30 mg |
| Vitamin B$_6$ | 13.0–23.0 mcg |
| Biotin | 0.43–0.73 mcg |
| Folic Acid | 3.5–6.5 mcg |
| Vitamin B$_{12}$ | 35.0–65.0 ng |
| Vitamin C | 3.5–6.5 mg. |

2. A nutritional composition as defined in claim 1, which includes the following minerals in weight percent:

| | |
|---|---|
| Sodium | 7.64–13.53 |
| Potassium | 24.12–40.58 |
| Magnesium | 1.47–2.94 |
| Calcium | 15.88–26.47 |
| Manganese | 0.00061–0.00205 |
| Iron | 0.021–0.0588 |
| Cobalt | 0.00058–0.0011 |
| Zinc | 0.020–0.038 |
| Nickel | 0.094–0.164 |
| Chromium | 0.00044–0.0014 |
| Molybdenum | 0.029–0.050 |
| Vanadium | 0.00041–0.0029 |
| Phosphorous | 0.00020–0.00038 |
| Chloride | 6.471–20.590 |
| Fluoride | 17.649–29.415 |
| Iodine | 0.007–0.012 |
| Selenium | 0.0023–0.0046 |
| Bromine | 0.0011–0.0026 |
| Boron | 0.041–0.076 |
| Silicon | 0.0023–0.0047. |

3. A nutritional composition as defined in claim 1 wherein in the Net Nitrogen Utilization is at least 90%.

4. A nutritional composition as defined in claim 1 which comprises in grams per 10 grams of composition:
 (a) from 1.217 to 1.647 isoleucine;
 (b) from 1.827 to 2.735 leucine;
 (c) from 1.260 to 2.359 lysine;
 (d) form 0.232 to 0.778 methionine;
 (e) from 0.843 to 1.314 phenylalanine;
 (f) from 0.970 to 1.287 threonine;
 (g) from 0.208 to 0.467 tryptophan; and
 (h) from 1.260 to 1.900 valine.

5. A nutritional composition as defined in claim 3 wherein the carbohydrate and highly polyunsaturated vegetable fat comprise from 12Kcal to 60Kcal per gram of amino acids.

6. A nutritional composition comprising a combination of the following essential amino acids:
 isoleucine;
 leucine;
 lysine;
 methionine;
 phenylalanine;
 threonine;
 tryptophan; and
 valine,
in amounts relative to one another which will provide a net nitrogen utilization of at least 80%.

7. A nutritional composition as defined in claim 5, which includes vitamins.

8. A nutritional composition as defined in claim 6, which includes minerals.

9. A nutritional composition as defined in claim 7, which also includes a source of carbohydrate and polyunsaturated vegetable fat.

10. A nutritional composition which comprises in grams per 10 grams of composition:
 (a) from 1.217 to 1.647 isoleucine;
 (b) from 1.827 to 2.735 leucine;
 (c) from 1.260 to 2.359 lysine;
 (d) from 0.232 to 0.778 methionine;
 (e) from 0.843 to 1.314 phenylalanine;
 (f) from 0.970 to 1.287 threonine;
 (g) from 0.208 to 0.467 tryptophan; and
 (h) from 1.260 to 1.900 valine.

11. A nutritional composition as defined in claim 10, which also includes vitamins.

12. A nutritional composition as defined in claim 10, which also includes a source of carbohydrate and a polyunsaturated vegetable fat.

13. A method of providing nutrition which comprises orally administered to a human patient an effective amount of the composition of claim 1.

14. A method of providing nutrition which comprises orally administering to a human patient an effective amount of the composition of claim 8.

15. A method of treating obesity which comprises orally administering to a human obese patient an effective amount of the composition of claim 7.

16. A method of treating obesity which comprises orally administering to a human obese patient an effective amount of the composition of claim 8.

17. A method of providing nutrition to a human patient who requires a restricted nitrogen intake, said method comprising orally administering an effective amount of the composition of claim 1.

18. A method of providing nutrition to a human patient who requires a low residue diet, said method comprising administering as effective amount of the composition of claim 1.

19. A method of providing nutrition to a human patient afflicted with acquired immune deficiency syndrome (AIDS) or acquired immune deficiency related complex, (ARC) said method comprising orally administering an effective amount of the composition of claim 8.

20. A nutritional composition which comprises:
 (a) from 70-95 wt. % of a protein-free carbohydrate selected from the group consisting of maltose, sucrose and sorbitol;
 (b) from 5-30 wt % of a protein-free highly unsaturated vegetable fat selected from the group consisting of safflower oil, sunflower oil and corn oil.

21. A vitamin composition which comprises the following vitamins in weight percent:

| | |
|---|---|
| Vitamin A | 0.036–0.063 |
| Vitamin D | 0.000021–0.00003 |
| Alpha-tocophrol | 0.229–0.382 |
| Vitamin K | 0.229–0.382 |
| Vitamin $B_1$ | 0.0011–0.0023 |
| Vitamin $B_2$ | 0.0058–0.0117 |
| Nicotinamide | 0.015–0.028 |
| Pantothenic acid | 0.076–0.135 |
| Vitamin $B_6$ | 0.105–0.176 |
| Brotin | 0.0076–0.013 |
| Folic Acid | 0.00025–0.0006 |
| Vitamin $B_{12}$ | 0.0020–0.0038 |
| Vitamin C | 0.000020–0.00003 |
| | 2.05–3.82 |

22. A nutritional composition comprising which consists essentially of a combination of the following:
 (a) isoleucine, leucine, lysine, methionine, phenylalanine, threonine, tryptophan, and valine in amounts relative to one another which will provide a Net Nitrogen Utilization (NNU) of at least 80%;
 (b) a carbohydrate selected from the group consisting of sucrose, maltose and sorbitol, and a highly polyunsaturated vegetable fat selected from the group consisting of safflower oil, sunflower oil and corn oil; and
 (c) for each gram of amino acid, an amount of vitamins which is equivalent to the following:

| | |
|---|---|
| Vitamin A | 60.0–109.0 mcg |
| Vitamin D | 37.0–63.0 ng |
| Alpha-tocopherol | 0.078–0.130 mg |
| Vitamin K | 2.0–4.0 mcg |
| Vitamin $B_1$ | 10.0–20.0 mcg |
| Vitamin $B_2$ | 27.0–48.0 mcg |
| Nicotinamide | 0.13–0.23 mg |
| Pantothenic Acid | 0.18–0.30 mg |
| Vitamin $B_6$ | 13.0–23.0 mcg |
| Biotin | 0.43–0.73 mcg |
| Folic Acid | 3.5–6.5 mcg |
| Vitamin $B_{12}$ | 35.0–65.0 ng |
| Vitamin C | 3.5–6.5 mg. |

23. A nutritional composition as defined in claim 1 which consists essentially of in grams per 10 grams of composition:
(a) from 1.217 to 1.647 isoleucine;
(b) from 1.827 to 2.735 leucine;
(c) from 1.260 to 2.359 lysine;
(d) from 0.232 to 0.778 methionine;
(e) from 0.843 to 1.314 phenylalanine;
(f) from 0.970 to 1.287 threonine;
(g) from 0.208 to 0.467 tryptophan; and
(h) from 1.260 to 1.900 valine.

24. A nutritional composition which consists essentially of in grams per 10 grams of composition:
(a) from 1.217 to 1.647 isoleucine;
(b) from 1.827 to 2.735 leucine;
(c) form 1.260 to 2.359 lysine;
(d) from 0.232 to 0.778 methionine;
(e) from 0.843 to 1.314 phenylalanine;
(f) from 0.970 to 1.287 threonine;
(g) from 0.208 to 0.467 tryptophan; and
(h) from 1.260 to 1.900 valine.

* * * * *